US012226444B2

(12) United States Patent
Muller

(10) Patent No.: US 12,226,444 B2
(45) Date of Patent: *Feb. 18, 2025

(54) COMPOSITIONS COMPRISING PEPTIDES COMPRISING VARIANT KINESIN LIGHT CHAIN 1 AND CELL-PENETRATING PEPTIDES

(71) Applicant: Northwestern University, Evanston, IL (US)

(72) Inventor: William A. Muller, Evanston, IL (US)

(73) Assignee: Northwestern University, Evasnton, IL (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/692,471

(22) Filed: Mar. 11, 2022

(65) Prior Publication Data

US 2022/0193182 A1 Jun. 23, 2022

Related U.S. Application Data

(63) Continuation of application No. 16/256,752, filed on Jan. 24, 2019, now Pat. No. 11,304,988.

(60) Provisional application No. 62/621,227, filed on Jan. 24, 2018.

(51) Int. Cl.
*A61K 38/08* (2019.01)
*A61P 35/04* (2006.01)

(52) U.S. Cl.
CPC .............. *A61K 38/08* (2013.01); *A61P 35/04* (2018.01)

(58) Field of Classification Search
CPC ..................................................... A61K 38/08
See application file for complete search history.

(56) References Cited

U.S. PATENT DOCUMENTS

| 4,816,567 | A | 3/1989 | Cabilly et al. | |
|---|---|---|---|---|
| 4,946,778 | A | 8/1990 | Ladner et al. | |
| 5,260,203 | A | 11/1993 | Ladner et al. | |
| 11,304,988 | B2* | 4/2022 | Muller | A61K 38/08 |
| 2008/0025958 | A1 | 1/2008 | Hannon et al. | |
| 2014/0243390 | A1 | 8/2014 | Downing et al. | |
| 2016/0237428 | A1 | 8/2016 | Sharp | |
| 2017/0198290 | A1* | 7/2017 | Muller | A61K 31/713 |

FOREIGN PATENT DOCUMENTS

WO WO 1988/01649 3/1988

OTHER PUBLICATIONS

Francesca Milletti, Drug Discovery Today, vol. 17, Nos. 15/16, Aug. 2012, pp. 850-860 (Year: 2012).*

Aizawa, H. et al. Kinesin family in murine central nervous system. J Cell Biol. Dec. 1992;119(5):1287-96.
Allmendinger, T. et al., Fluoroolefin Dipeptide Isosteres. Tetrahydron Lett., 1990; 50, pp. 7297-7300.
Anisman, H, et al. Neuroimmune mechanisms in health and disease: 2. Disease. CMAJ. Oct. 15, 1996;155(8):1075-82.
Aragon-Sanabria, V, et al. VE-Cadherin Disassembly and Cell Contractility in the Endothelium are Necessary for Barrier Disruption Induced by Tumor Cells. Sci Rep. Apr. 10, 2017;7:45835. doi: 10.1038/srep45835.
Bloom, GS, et al. Native structure and physical properties of bovine brain kinesin and identification of the ATP-binding subunit polypeptide. Biochemistry. May 3, 1988;27(9):3409-16.
Butcher, EC. Leukocyte-endothelial cell recognition: three (or more) steps to specificity and diversity. Cell. Dec. 20, 1991;67(6):1033-6.
Chorev, M. et al., A Dozen Years of Retro-Inverso Peptidomimetics. Acc. Chem. Res, 1993, 26, 266.
Clackson et al. Making antibody fragments using phage display libraries. Nature. Aug. 15, 1991;352(6336):624-8.
Cole, DG, et al. Novel heterotrimeric kinesin-related protein purified from sea urchin eggs. Nature 1993, 366:268-70.
Cyr, JL, et al. Molecular genetics of kinesin light chains: generation of isoforms by alternative splicing. Proc Natl Acad Sci U S A. Nov. 15, 1991;88(22):10114-8.
Cyrus, BF, et al. A Unique Role for Endothelial Cell Kinesin Light Chain 1, Variant 1 in Leukocyte Transendothelial Migration. Am J Pathol. May 2016;186(5):1375-86.
Daire, V, et al. Kinesin-1 regulates microtubule dynamics via a c-Jun N-terminal kinase-dependent mechanism. J Biol Chem. Nov. 13, 2009;284(46):31992-2001.
Dasgupta, B, et al. A novel and critical role for tyrosine 663 in PECAM trafficking and transendothelial migration. J Immunol. Apr. 15, 2009;182(8):5041-51.
Diefenbach RJ, et al. The C-terminal region of the stalk domain of ubiquitous human kinesin heavy chain contains the binding site for kinesin light chain. Biochemistry. Nov. 24, 1998;37(47):16663-70.
Elbashir, et al. RNA interference is mediated by 21- and 22-nucleotide RNAs. Genes Dev. Jan. 15, 2001;15(2):188-200.
Elbashir, et al., Duplexes of 21-nucleotide RNAs mediate RNA interference in cultured mammalian cells. Nature. May 24, 2001;411(6836):494-8.
Feng, D, et al. Vesiculo-vacuolar organelles and the regulation of venule permeability to macromolecules by vascular permeability factor, histamine, and serotonin. J Exp Med. May 1, 1996;183(5):1981-6.
Feng, G, et al. Segregation of VE-cadherin from the LBRC depends on the ectodomain sequence required for homophilic adhesion. J Cell Sci. Feb. 1, 2015;128(3):576-88.
Fidler, IJ. Metastasis: quantitative analysis of distribution and fate of tumor emboli labeled with 125 I-5-iodo-2'-deoxyuridine. J Natl Cancer Inst. Oct. 1970;45(4):773-82.
Gindhart, JG, Jr., et al. Kinesin light chains are essential for axonal transport in *Drosophila*. J Cell Biol. Apr. 20, 1998;141(2):443-54.

(Continued)

*Primary Examiner* — Melissa L Fisher
*Assistant Examiner* — Joseph Fischer
(74) *Attorney, Agent, or Firm* — David W. Staple; Casimir Jones, S.C.

(57) ABSTRACT

Provided herein are compositions and methods for inhibiting tumor cell transendothelial migration by inhibition of kinesin light chain 1, variant 1 (KLC1C) expression and/or activity, and treatment or prevention of cancer and/or metastasis therewith.

12 Claims, 20 Drawing Sheets

Specification includes a Sequence Listing.

(56) References Cited

OTHER PUBLICATIONS

Gindhart, JG, Jr., et al. Tetratrico peptide repeats are present in the kinesin light chain. Trends Biochem Sci. Feb. 1996;21(2):52-3.

Glater, EE, et al. Axonal transport of mitochondria requires milton to recruit kinesin heavy chain and is light chain independent. J Cell Biol. May 22, 2006;173(4):545-57.

Gyoeva, FK, et al. An isoform of kinesin light chain specific for the Golgi complex. J Cell Sci. Jun. 2000;113 ( Pt 11):2047-54.

Harlow E. et al., 1988, Antibodies: A Laboratory Manual (Cold Spring Harbor Laboratory, Cold Spring Harbor, N.Y.).

Hirokawa, N, et al. Kinesin superfamily motor proteins and intracellular transport. Nat Rev Mol Cell Biol. Oct. 2009;10(10):682-96.

Hirokawa, N, et al. Submolecular domains of bovine brain kinesin identified by electron microscopy and monoclonal antibody decoration. Cell. Mar. 10, 1989;56(5):867-78.

Hirokawa, N, From electron microscopy to molecular cell biology, molecular genetics and structural biology: intracellular transport and kinesin superfamily proteins, KIFs: genes, structure, dynamics and functions. J Electron Microsc (Tokyo). 2011;60 Suppl 1:S63-92.

Hoffman, R. V. et al. The Stereoselective Synthesis of 2-Alkyl.gamma.-Keto Acid and Heterocyclic Ketomethylene Peptide Isostere Core Units Using Chiral Alkylation by 2-Triflyloxy Esters. J. Org. Chem., 1995;60(16):5107-5113.

Homey B, et al. Chemokines: agents for the immunotherapy of cancer? Nat Rev Immunol. Mar. 2002;2(3):175-84.

Hudson PJ, Engineered antibodies. Nat Med. Jan. 2003; 9(1):129-34.

Ingold, AL, et al. Inhibition of kinesin-driven microtubule motility by monoclonal antibodies to kinesin heavy chains. J Cell Biol. Dec. 1988;107(6 Pt 2):2657-67.

Inomata H, et al. A scaffold protein JIP-1b enhances amyloid precursor protein phosphorylation by JNK and its association with kinesin light chain 1. J Biol Chem. Jun. 20, 2003;278(25):22946-55.

Jaulin, F. et al. Polarization-dependent selective transport to the apical membrane by KIF5B in MDCK cells. Dev Cell. Oct. 2007;13(4):511-22.

Junco A, et al. Kinesin light-chain KLC3 expression in testis is restricted to spermatids. Biol Reprod. May 2001;64(5):1320-30.

Kamal, A. et al. Axonal transport of amyloid precursor protein is mediated by direct binding to the kinesin light chain subunit of kinesin-I. Neuron. Nov. 2000;28(2):449-59.

Kanai Y, et al. KIF5C, a novel neuronal kinesin enriched in motor neurons. J Neurosci. Sep. 1, 2000;20(17):6374-84.

Khodjakov, A, et al. A specific light chain of kinesin associates with mitochondria in cultured cells. Mol Biol Cell. Feb. 1998;9(2):333-43.

Köhler et al., Continuous cultures of fused cells secreting antibody of predefined specificity. Nature. Aug. 7, 1975;256(5517):495-7.

Krogsgaard et al. (Eds) 1996, Horwood Acad. "Drug Design and Development" Chapter. 14.

Krylyshkina, O, et al. Modulation of substrate adhesion dynamics via microtubule targeting requires kinesin-1. J Cell Biol. Jan. 21, 2002;156(2):349-59.

Lavielle, S. et al., Importance of the leucine side-chain to the spasmogenic activity and binding of substance P analogues. Int J Pept Protein Res. Sep. 1993;42(3):270-7.

Lawrence CJ, et al. A standardized kinesin nomenclature. J Cell Biol. Oct. 11, 2004;167(1):19-22.

Ley K, et al. Getting to the site of inflammation: the leukocyte adhesion cascade updated. Nat Rev Immunol. Sep. 2007;7(9):678-89.

Li B, et al. Involvement of Rho/ROCK signalling in small cell lung cancer migration through human brain microvascular endothelial cells. FEBS Lett. Jul. 24, 2006;580(17):4252-60.

Liao F, et al. Migration of monocytes across endothelium and passage through extracellular matrix involve separate molecular domains of PECAM-1. J Exp Med. Nov. 1, 1995;182(5):1337-43.

Liao G. Kinesin is a candidate for cross-bridging microtubules and intermediate filaments. Selective binding of kinesin to detyrosinated tubulin and vimentin. J Biol Chem. Apr. 17, 1998;273(16):9797-803.

Luisi, G et al. ψ(SO2-NH) transition state isosteres of peptides. Synthesis of the glutathione disulfide analogue. Tetrahedron Lett. 1993;34(14), 2391-2392.

Mamdouh Z, et al. Targeted recycling of PECAM from endothelial cell surface-connected compartments during diapedesis. Nature. Feb. 13, 2003;421(6924):748-53.

Mamdouh Z, et al. Transcellular migration of leukocytes is mediated by the endothelial lateral border recycling compartment. J Exp Med. Nov. 23, 2009;206(12):2795-808.

Mamdouh Z, et al . . . Leukocyte transmigration requires kinesin-mediated microtubule-dependent membrane trafficking from the lateral border recycling compartment. J Exp Med. Apr. 14, 2008;205(4):951-66.

Marks, JD et al. By-passing immunization: Human antibodies from V-gene libraries displayed on phage. J Mol Biol. Dec. 5, 1991;222(3):581-97.

McCart, AE, et al. Alternatively spliced products of the human kinesin light chain 1 (KNS2) gene. Traffic. Aug. 2003;4(8):576-80.

Miki et al., Analysis of the kinesin superfamily: insights into structure and function. Trends Cell Biol. Sep. 2005;15(9):467-76.

Morihara T, et al. Transcriptome analysis of distinct mouse strains reveals kinesin light chain-1 splicing as an amyloid-beta accumulation modifier. Proc Natl Acad Sci U S A. Feb. 18, 2014;111(7):2638-43.

Muller WA, et al. A human endothelial cell-restricted, externally disposed plasmalemmal protein enriched in intercellular junctions. J Exp Med. Aug. 1, 1989;170(2):399-414.

Muller WA, et al. Monocyte-selective transendothelial migration: Dissection of the binding and transmigration phases by an in vitro assay. J Exp Med. Sep. 1, 1992;176(3):819-28.

Muller WA, et al. PECAM-1 is required for transendothelial migration of leukocytes. J Exp Med. Aug. 1, 1993;178(2):449-60.

Muller WA, Luscinskas FW. Assays of transendothelial migration in vitro. Methods Enzymol. 2008;443:155-76.

Muller WA. Localized signals that regulate transendothelial migration. Curr Opin Immunol. Feb. 2016;38:24-9.

Muller WA. Mechanisms of leukocyte transendothelial migration. Annu Rev Pathol. 2011;6:323-44.

Niclas J, et al. Cloning and localization of a conventional kinesin motor expressed exclusively in neurons. Neuron. May 1994;12(5):1059-72.

Ostresh, J. M. et al. "Libraries from libraries": chemical transformation of combinatorial libraries to extend the range and repertoire of chemical diversity. Proc Natl Acad Sci U S A. Nov. 8, 1994;91(23):11138-42.

Rahman A, et al. Two kinesin light chain genes in mice. Identification and characterization of the encoded proteins. J Biol Chem. Jun. 19, 1998;273(25):15395-403.

Rice SE, et al. Paradigm lost: milton connects kinesin heavy chain to miro on mitochondria. J Cell Biol. May 22, 2006;173(4):459-61.

Rodionov, VI, et al. Kinesin is responsible for centrifugal movement of pigment granules in melanophores. Proc Natl Acad Sci U S A. Jun. 1, 1991;88(11):4956-60.

Sasaki, Y et al. Protection of w(CH2NH) Peptide Bond with 2,4-Dimethoxybenzyl Group in Solid-Phase Peptide Synthesis. Chem. Pharm. Bull. 1997; 45(1),13-17.

Saxena, M, et al. Rebuilding cancer metastasis in the mouse. Mol Oncol. Apr. 2013;7(2):283-96.

Schmidt, R. et al., Structure-activity relationships of dermorphin analogues containing N-substituted amino acids in the 2-position of the peptide sequence. Int J Pept Protein Res. Jul. 1995;46(1):47-55.

Sherman, D. B. et al. Compatibility of Thioamides with Reverse Turn Features: Synthesis and Conformational Analysis of Two Model Cyclic Pseudopeptides Containing Thioamides as Backbone Modifications. Am. Chem. Soc., 1990;112:433-441.

Spatola, A. F. Synthesis of Pseudopeptides. Methods Neurosci, 1993;13: 19-42.

Strilic B, et al. Intravascular Survival and Extravasation of Tumor Cells. Cancer Cell. Sep. 11, 2017;32(3):282-293.

(56) References Cited

OTHER PUBLICATIONS

Strilic B, et al. Tumour-cell-induced endothelial cell necroptosis via death receptor 6 promotes metastasis. Nature. Aug. 11, 2016;536(7615):215-8.

Sullivan DP, et al. Neutrophil and monocyte recruitment by PECAM, CD99, and other molecules via the LBRC. Semin Immunopathol. Mar. 2014;36(2):193-209.

Sullivan DP, et al. Poliovirus receptor (CD155) regulates a step in transendothelial migration between PECAM and CD99. Am J Pathol. Mar. 2013;182(3):1031-42.

Tincu et al., Antimicrobial peptides from marine invertebrates. Antimicrob Agents Chemother. Oct. 2004;48(10):3645-54.

Tuschl T, et al., Targeted mRNA degradation by double-stranded RNA in vitro. Genes Dev. Dec. 15, 1999;13(24):3191-7.

Van Ziji et al., Initial steps of metastasis: cell invasion and endothelial transmigration. Mutat Res. Jul.-Oct. 2011;728(1-2):23-34.

Vicente et al., Mitosis, microtubule dynamics and the evolution of kinesins. Exp Cell Res. May 15, 2015;334(1):61-9.

Watson RL, et al. Endothelial CD99 signals through soluble adenylyl cyclase and PKA to regulate leukocyte transendothelial migration. J Exp Med. Jun. 29, 2015;212(7):1021-41.

Weber EW, et al. TRPC6 is the endothelial calcium channel that regulates leukocyte transendothelial migration during the inflammatory response. J Exp Med. Oct. 19, 2015;212(11):1883-99.

Wedaman KP, et al. Sequences of sea urchin kinesin light chain isoforms. J Mol Biol. May 5, 1993;231(1):155-8.

Wiley HE, et al. Expression of CC chemokine receptor-7 and regional lymph node metastasis of B16 murine melanoma. J Natl Cancer Inst. Nov. 7, 2001;93(21):1638-43.

Winger RC, et al. Rapid remodeling of tight junctions during paracellular diapedesis in a human model of the blood-brain barrier. J Immunol. Sep. 1, 2014;193(5):2427-37.

Wong SY, et al. 2006. Lymphatic or hematogenous dissemination: how does a metastatic tumor cell decide? Cell cycle.5(8):812-7. PMCID:1459485.

Woźniak MJ, et al. Cargo selection by specific kinesin light chain 1 isoforms. EMBO J. Nov. 29, 2006;25(23):5457-68.

Wright SD, et al., Identification of the C3bi receptor of human monocytes and macrophages by using monoclonal antibodies. Proc Natl Acad Sci U S A. Sep. 1983;80(18):5699-703.

Zen K, et al. Leukocyte-epithelial interactions. Curr Opin Cell Biol. Oct. 2003;15(5):557-64.

International Search Report and Written Opinion for PCT/US2019/014968, mailed Sep. 13, 2019, 11 pages.

* cited by examiner

FIG. 2

YGRKKRRQRRR GGG MRKMKLGLVN KLC1c
GKLNKMVMLR scrambled

Tat        Linker

COMPOSITIONS COMPRISING PEPTIDES COMPRISING VARIANT KINESIN LIGHT CHAIN 1 AND CELL-PENETRATING PEPTIDES

CROSS-REFERENCE TO RELATED APPLICATIONS

The present application is a continuation of U.S. patent application Ser. No. 16/256,752, filed Jan. 24, 2019, which claims priority to U.S. Provisional Patent Application No. 62/621,227, filed Jan. 24, 2018, each of which is incorporated by reference in its entirety.

FIELD

Provided herein are compositions and methods for inhibiting tumor cell transendothelial migration by inhibition of kinesin light chain 1, variant 1 (KLC1C) expression and/or activity, and treatment or prevention of cancer and/or metastasis therewith.

BACKGROUND

Most deaths from solid tumors are due to metastases-cancer cells breaking off the primary tumor, traveling to distant parts of the body and establishing new growths there (Refs. B1-B3; herein incorporated by reference in their entireties). Patients with cancer shed millions of circulating tumor cells (CTCs) into their bloodstream every day. There is a good deal known about how malignant cells break away from the primary tumor and move through connective tissue into lymphatics and blood vessels. Almost all CTCs die in the vasculature or are eliminated by the body's inflammatory response (Refs. B1, B4; herein incorporated by reference in their entireties). However, those tumor cells that manage to extravasate out of the bloodstream and into tissues have the potential to grow as metastatic colonies that spread the cancer far beyond the primary site. Unfortunately, there is almost nothing known about this step.

Transendothelial migration (TEM) (ref. A1-A3; herein incorporated by reference in their entireties) refers to a mechanism by which cells, particularly leukocytes, move from the vasculature in to adjacent tissues. This occurs most often at endothelial cell borders (paracellular migration). The lateral border recycling compartment (LBRC) is membrane compartment in endothelial cells that regulates TEM (refs. A5-A11; herein incorporated by reference in their entireties).

SUMMARY

Provided herein are compositions and methods for inhibiting tumor cell transendothelial migration by inhibition of kinesin light chain 1, variant 1 (KLC1C) expression and/or activity, and treatment or prevention of cancer and/or metastasis therewith.

In some embodiments, provided herein are methods of preventing or reducing the likelihood of metastasis in a subject comprising administering to the subject an agent that inhibits the binding of kinesin light chain 1, variant 1 (KLC1C) to its cargo. In some embodiments, administering said agent inhibits transendothelial migration (TEM) of tumor cells. In some embodiments, administering said agent inhibits targeted recycling of the lateral border recycling compartment (LBRC). In some embodiments, the agent prevents or reduces the expression of KLC1C. In some embodiments, the agent is a nucleic acid. In some embodiments, the agent is an shRNA, siRNA, or antisense oligonucleotide. In some embodiments, the agent inhibits binding of KLC1C to its cargo. In some embodiments, the agent is a peptide, antibody, or small molecule. In some embodiments, the agent is soluble, cell-permeable, and biocompatible. In some embodiments, the subject suffers from cancer. In some embodiments, the cancer is a solid tumor cancer. In some embodiments, the subject is in remission from cancer. In some embodiments, the cancer is a solid tumor cancer. In some embodiments, methods further comprise administering a second cancer therapeutic or therapy to the subject. In some embodiments, the second cancer therapeutic or therapy is selected from an immunotherapy, a chemotherapy, radiation, and surgery. In some embodiments, the agent is administered systemically or locally. In some embodiments, the agent is administered to endothelial or epithelial cells. In some embodiments, the agent is administered to the blood and/or vasculature. In some embodiments, the agent is a peptide, polypeptide, or peptidomimetic that competes with KLC1C for binding to its cargo. In some embodiments, the agent comprises an amino acid sequence having at least 70% sequence identity to SEQ ID NO: 1. In some embodiments, the agent comprises an amino acid sequence having at least 80% sequence similarity to SEQ ID NO: 1. In some embodiments, the agent comprises an amino acid sequence comprising SEQ ID NO: 1.

BRIEF DESCRIPTION OF THE DRAWINGS

FIG. 2. Exemplary cell-permeable peptides used in experiments herein aligned in single letter code. The 11-amino acid basic region from HIV Tat protein is separated by a glycine tripeptide linker from the C-terminal decapeptide of KLC1c derived by splicing in of exon 14 (SEQ ID NO: 8). The negative control peptide contains the same ten amino acids in a random order (scrambled, Scr) (SEQ ID NO: 9).

FIG. 14. B16F10 cells in lung of mice treated with Tat-Scr 5 days after injection. 25% of the tumor cells were seen several cell diameters away from leukocytes stained with anti CD11a.

DEFINITIONS

Figure 1:
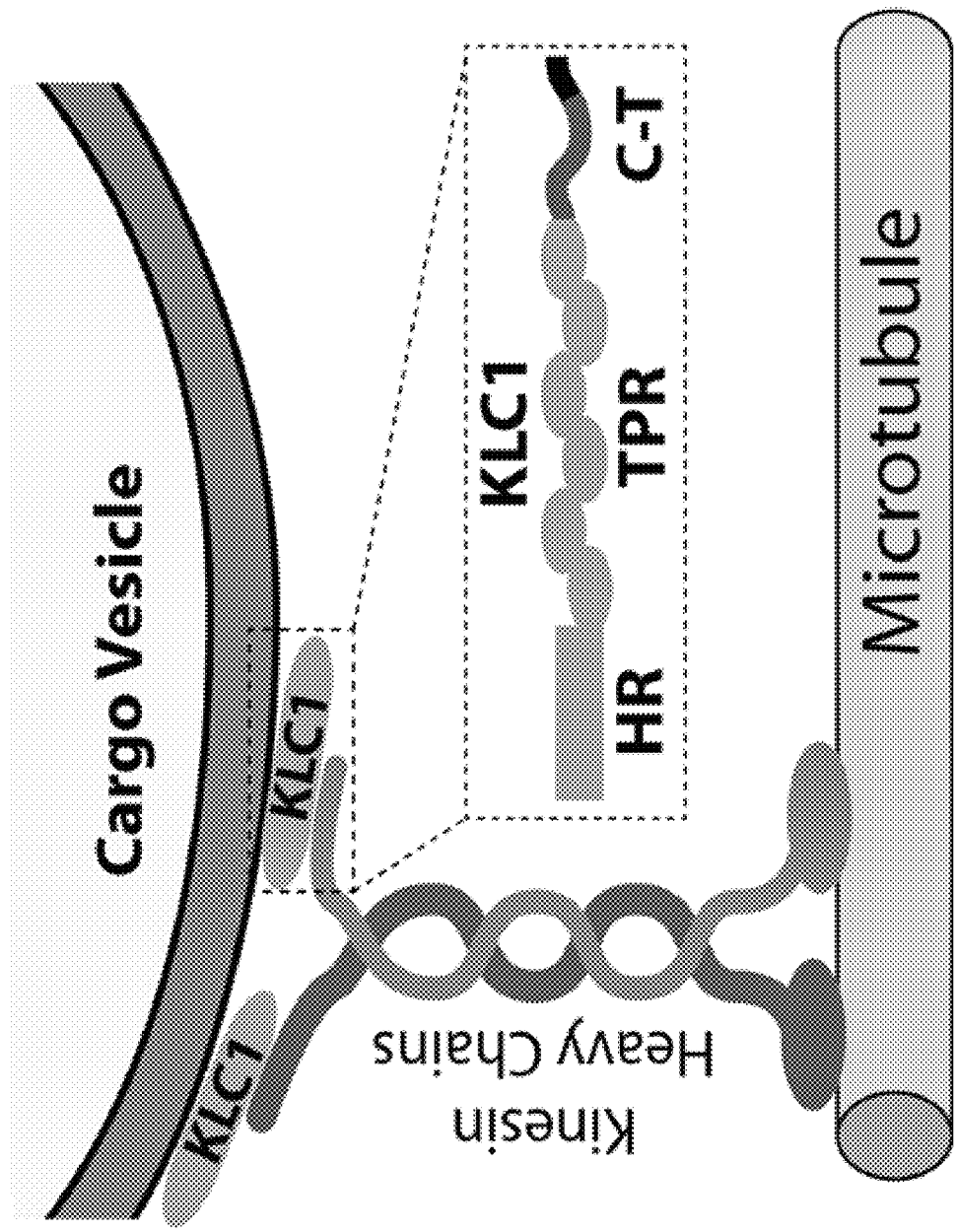
FIG. 1. Representation of kinesin-1 and KLC1 moving cargo along microtubule. KLC1 binds to kinesin heavy chain through its heptad repeat (HR) region. The 6 tetratricopeptide repeats (TPR) assist in binding cargo, but the variable C terminal (C-T) domain confers the specificity of binding through alternative splicing.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular embodiments, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the terms "kinesin-1 inhibitor," "KLC inhibitor," "KLC1C inhibitor," or linguistic variants thereof (e.g., "inhibitor of KLC1C," "KLC1C inhibiting agent," etc.) refer to an agent that attenuates the expression of kinesin-1, KLC, or KLC1C, respectively (e.g., interferes with gene expression), including suppression of transcription or translation; and/or an agent that directly inhibits kinesin-1, KLC, or KLC1C activity (e.g., cargo binding), for example by binding to kinesin-1, KLC, or KLC1C, respectively.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated for a disease or condition or prophylactically.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-cthylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers to a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" refers to a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature) or may be a peptide that is not a subsequence of a naturally occurring protein or polypeptide. For example, a "mutant C-terminal KLC1C peptide" may be a subsequence of a naturally-occurring, non-wild-type C-terminal KLC1C peptide, or may be distinct sequence not found in naturally-occurring KLC1C polypeptides.

As used herein, the term "artificial peptide" or "artificial polypeptide" refers to a peptide or polypeptide having a distinct amino acid sequence from those found in natural peptides and/or proteins. An artificial protein is not a subsequence of a naturally occurring protein, either the wild-type (i.e., most abundant) or mutant versions thereof. For example, an artificial KLC1C c-terminal peptide is not a subsequence of naturally occurring KLC1C. An artificial peptide or polypeptide may be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimitecs include chemically modified peptides, peptoids (side chains are appended to the nitrogen atom of the peptide backbone, rather than to the α-carbons), β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine(S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine(S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "antibody" refers to a whole antibody molecule or a fragment thereof (e.g., fragments such as Fab, Fab', and F(ab')2), unless otherwise specified (e.g., "full-length antibody," "antibody fragment," etc.). An antibody may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function. In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant (Ka) of at least $10^7$ $M^{-1}$ (e.g., >$10^7$ $M^{-1}$, >$10^8$ $M^{-1}$, >$10^9$ $M^{-1}$, >$10^{10}$ $M^{-1}$, >$10^{11}$ $M^{-1}$, >$10^{12}$ $M^{-1}$, >$10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. Sec, e.g., Kohler and Milstein (1975) Nature 256:495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. Sec, e.g., Clackson et al. (1991) Nature 352:624-628; and Marks et al. (1991) J. Mol. Biol. 222:581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')2, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the CH1 and CH2 domains. An interchain disulfide bond can be formed between two heavy chains of a Fab' fragment to form a "F(ab')2" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., cd., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition (e.g., cancer) as well as individuals who are at risk of acquiring a particular condition or disorder (e.g., those needing prophylactic/preventative measures). The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are compositions and methods for inhibiting tumor cell transendothelial migration by inhibition of kinesin light chain 1, variant 1 (KLC1C) expression and/or activity, and treatment or prevention of cancer and/or metastasis therewith.

Circulating tumor cells that get lodged in the microvasculature and are not rapidly eliminated, have the potential kill the surrounding endothelial cells by inducing ischemic necrosis or necroptosis (Ref. B3; herein incorporated by reference in its entirety), destroying the vascular barrier as they enter the tissues. The resulting tissue damage triggers the innate immune response to attack and destroy the invading tumor cells, thereby contributing to the inefficiency of the metastatic process. However, if tumor cells extravasate without triggering an inflammatory reaction, they would be able to establish colonies and a favorable microenvironment for growth. Leukocytes migrate across endothelial cells (EC) without increasing vascular permeability (Refs. B5, B6; herein incorporated by reference in their entireties) or inducing tissue damage. They do this through a series of molecular interactions with molecules on the endothelial cells that recruit membrane from a perijunctional organelle called the lateral border recycling compartment (LBRC) (Refs. B7-B9). Membrane from the LBRC increases the surface area of the junction allowing leukocytes to pass across without harming the EC or requiring them to retract and allow plasma leakage or exposure of basement membrane. Experiments were conducted during development of embodiments herein demonstrate that tumor cells, like leukocytes, recruit the LBRC to cross into tissues without triggering an inflammatory response, thereby favoring their survival to form a metastatic colony. Experiments conducted during development of embodiments herein also demonstrate that selective inhibition of LBRC movement blocks metastases in vitro and in vivo.

The LBRC is a reticulum of interconnected 50 nm vesicle-like structures that lies immediately below the plasma membrane at EC borders. It is distinct from other intracellular vesicular structures (Ref. B9; herein incorporated by reference in its entirety). Roughly a third of endothelial PECAM, CD99, and other molecules involved in TEM reside in the LBRC at any given moment and constitutively recycle to the plasma membrane with a half time of approximately 10 minutes (Refs. B8, B9, B13; herein incorporated by reference in their entireties). When a white blood cell (WBC) begins to transmigrate, membrane from the LBRC is directed along microtubules by kinesin motors to the site of TEM in a process called targeted recycling (Ref. B7; herein incorporated by reference in its entirety). This brings sufficient membrane and unligated PECAM, CD99, and other molecules involved in TEM from the LBRC to the site at which the WBC contacts the junction to facilitate its passage. Targeted recycling of the LBRC is essential for efficient TEM; anything that blocks targeted recycling of the LBRC inhibits TEM (Refs. B7-B9, B14; herein incorporated by reference in their entireties). Targeted recycling of the LBRC requires a specific kinesin heavy chain (kinesin 1) and specific kinesin light chain splice variant KLC1c (Ref. B15; herein incorporated by reference in its entirety) (FIG. 1). KLC1c differs from other forms of kinesin light chain by the C-terminal 10 amino acids (Refs.

Figure 3:
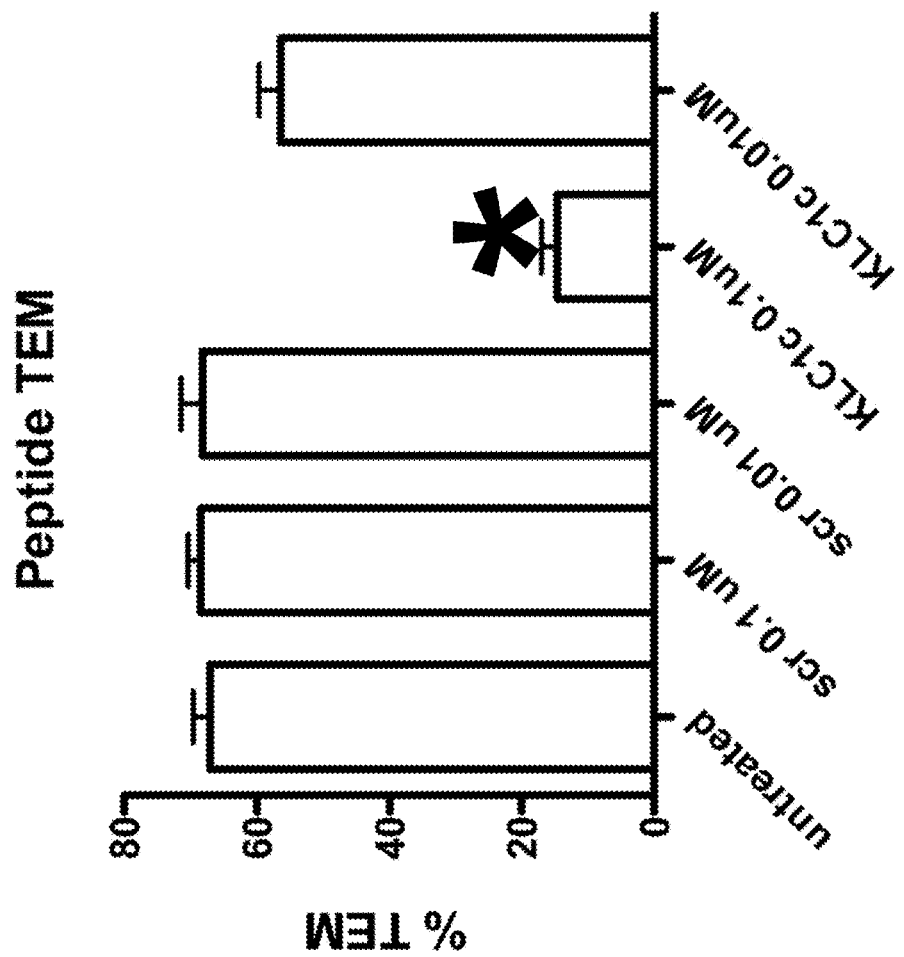
FIG. 3. Blocking Kinesin Light Chain 1c function via TAT-KLC1c peptide inhibits transmigration. Human umbilical vein endothelial cells. Endothelial cells were incubated for 30 minutes with either 0 µM (untreated), 0.01 µM, or 0.1 µM TAT-KLC1c peptide (or scrambled TAT-peptide) at 37° C., then washed prior to a one hour incubation with human monocytes. The cells were then washed, fixed, and the percentage of cells transmigrated (% TEM) was quantified. TAT-KLC1c, but not TAT-scrambled peptide, significantly decreased TEM. Data shown are mean±SEM for 3 experiments. *p<0.01 compared to untreated.
Figure 4:
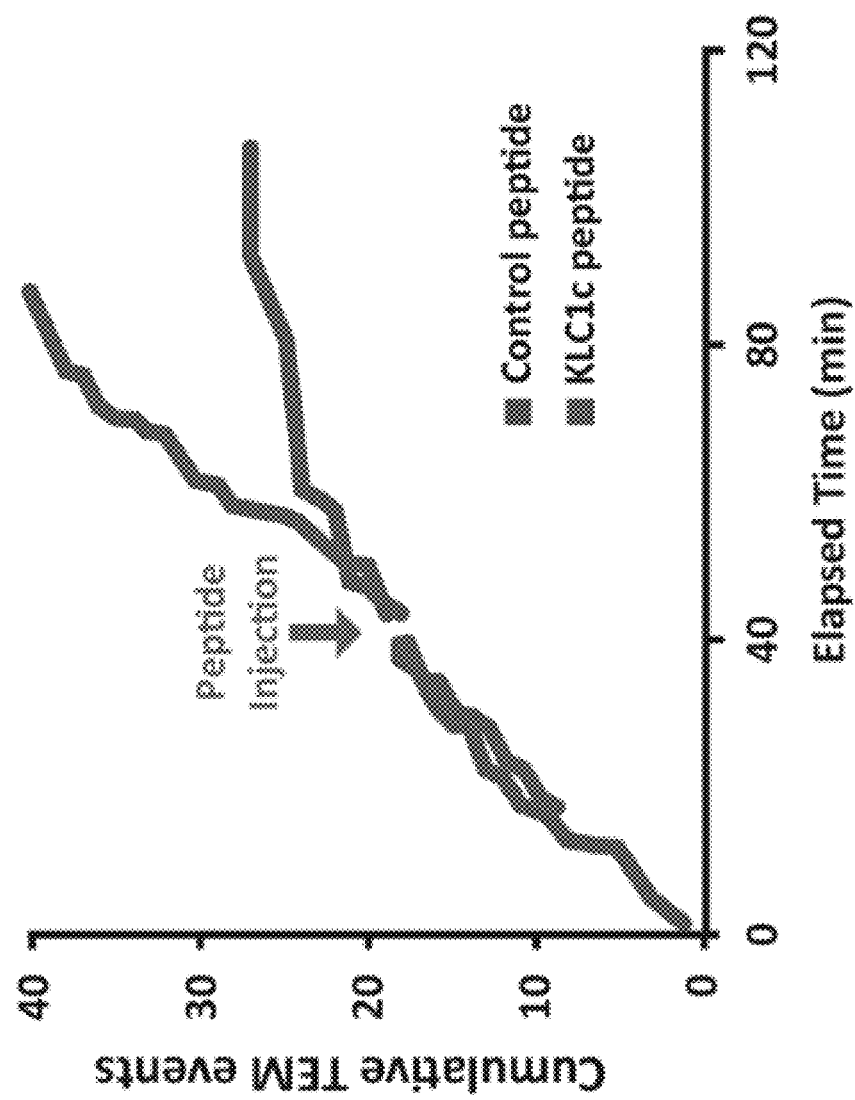
FIG. 4. TAT-KLC1c blocks TEM in vivo. In the inflamed cremaster muscle of an anesthetized mouse, fluorescent neutrophils were observed by intravital spinning disc confocal microscopy to transmigrate steadily from postcapillary venules in response to IL-1B. Within 10 minutes of injection of TAT-KLC1c decapeptide, cumulative transmigration began to plateau that is, neutrophil extravasation was markedly inhibited, while TAT-KLC1c scrambled peptide had no effect. Graph shows two experiments superimposed.
Figure 5:
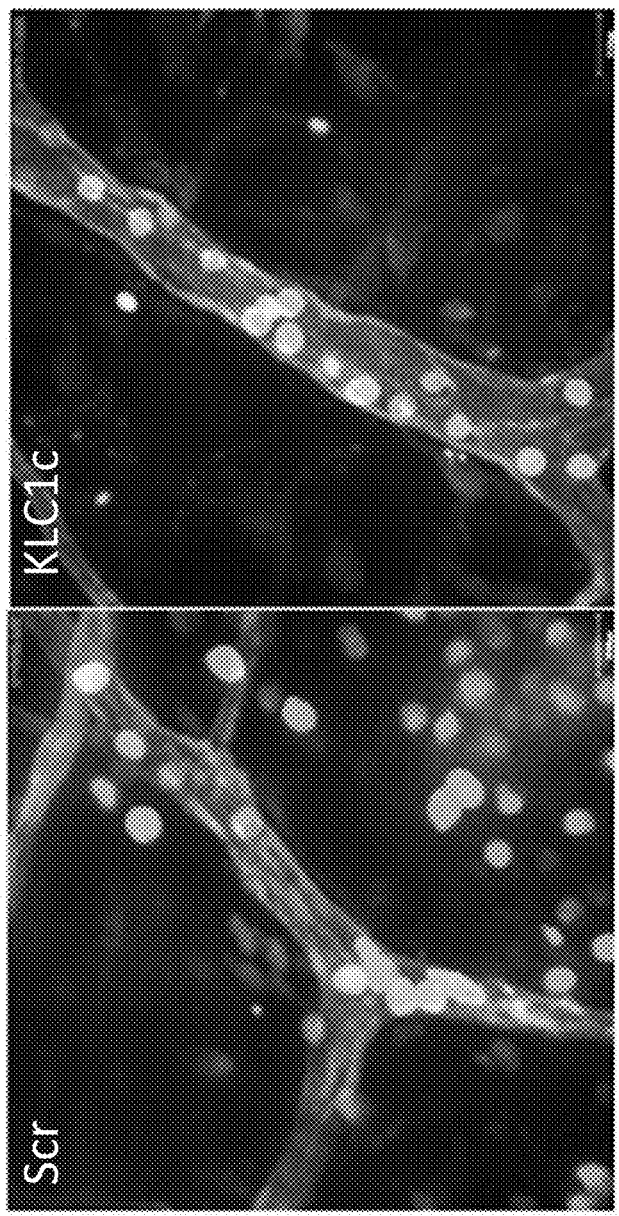
FIG. 5. TAT-KLC1c blocks TEM in vivo. Mice received TAT-Ser or TAT-KLC1c i.v. at a concentration to achieve 0.1 µM in blood. One hour later, croton oil was applied to mouse car skin to induce acute dermatitis. Six hours later mice were sacrificed and car skin examined in whole mount by confocal microscopy. Representative images are shown. In mice receiving Tat-Scr, a mean of 70% of PMN exited the vessels, while in mice receiving Tat-KLC1c, transmigration was decreased to 12%.

B16, B17; herein incorporated by reference in their entireties). A cell-permeable peptide containing this 10 amino acid sequence (FIG. 2) enters EC and blocks leukocyte TEM in vitro (FIG. 3) and in vivo (FIGS. 4-5), while the Tat-scrambled sequence enters cells but has no effect.

Kinesin (e.g., kinesin-1) is a tetrameric molecule composed of two heavy chains and two light chains, which transports various cargos along microtubules toward their plus ends. The heavy chains typically provide the motor activity, while the light chains bind to various cargos. Some cargoes may actually bind directly to the kinesin heavy chain, such as milton, which competes with light chains for binding to the heavy chain (refs A16-A17; herein incorporated by reference in their entireties). Kinesin light chains are composed of an α-helical coiled-coil heptad repeat domain that binds to the kinesin heavy chain, six imperfect tetratricopeptide repeats that mediate cargo-binding (refs. A39-A42; herein incorporated by reference in their entireties) and a variable C-terminal domain (ref. A38; herein incorporated by reference in its entirety). Known kinesin light chains include kinesin light chain 1 (KLC1), kinesin light chain 2 (KLC2), kinesin light chain 3 (KLC3), kinesin light chain 4 (KLC4). Kinesin light chain 1 (KLC1) is a protein that in humans is encoded by the KLC1 gene. Due to alternative splicing in this C-terminal domain, different KLC1 variants have been proposed to mediate binding to specific cargoes such as vimentin, mitochondria, and Golgi membranes (refs. A37, A43-A45; herein incorporated by reference in their entireties). Specifically, human KLC1 isoform variant E has been suggested to play a role in intracellular trafficking in amyloid-β accumulation (refs. A46-A48; herein incorporated by reference in their entireties). Amyloid-β accumulation is typical of Alzheimer's disease, and knocking down KLC1E in neuroblastoma cells decreased the levels of amyloid-β. Conversely, overexpression of this variant increased amyloid-β levels.

KLC1 isoform variant 1 (KLC1C) is critical for TEM. Kinesin heavy chains process along microtubules carrying bound cargo in the direction of the "plus" end. Kinesin light chains bind a restricted range of cargoes and tether them to kinesin heavy chains by binding to the carboxy terminal of the heavy chains. KLC1C is the link between Kinesin-1 and the LBRC cargo during TEM.

Experiments conducted during development of embodiments herein demonstrate that the KLC1C variant is a key factor in targeted recycling of the LBRC and transendothelial migration (TEM). Kinesin-1 complexes comprising this light chain variant (KLC1C) are responsible for migration of tumor cells from the vasculature into tissues, allowing metastasis while evading an immune response. In particular, the C-terminal peptide (SEQ ID NO: 1) of the KLC1C polypeptide (SEQ ID NO: 2) is responsible for the cargo specificity, and the role of KLC1C in TEM, targeted recycling of the LBRC, and/or migration of tumor cells from the vasculature into tissues.

Accordingly, some embodiments herein relate to targeting of KLC1C and/or its C-terminal peptide region (MRKMKLGLVN (SEQ ID NO: 1)) to inhibit TEM and targeted recycling of the LBRC and to prevent/reduce migration of tumor cells from the vasculature into tissues. In some embodiments, KLC1C expression is inhibited (e.g., siRNA, shRNA, etc.). In some embodiments, KLC1C binding to its cargo is inhibited (e.g., by a small molecule, peptide, antibody, etc.). In some embodiments, a polypeptide that mimics KLC1C (e.g., comprising SEQ ID NO: 2, comprising at least 70% sequence identity/similarity to SEQ ID NO: 2) is provided. In some embodiments, a peptide that mimics the C-terminal peptide of KLC1C (e.g., comprising SEQ ID NO: 1, comprising at least 70% sequence identity/similarity to SEQ ID NO: 1) is provided. In some embodiments, a synthetic KLC1C C-terminal peptide is provided to compete with endogenous KLC1C for cargo binding.

In some embodiments, compositions and methods described herein specifically target KLC1C for the inhibition of TEM and targeted recycling of the LBRC and to prevent/reduce migration of tumor cells from the vasculature into tissues, and thereby preventing/reducing metastasis. In some embodiments, other kinesins, kinesin-1 proteins, kinesin-1 light chain polypeptides, etc. are not targeted, are not affected, or are affected to a significantly lesser degree that KLC1C (e.g., <50%, <25%, <10%, <5%, <1%, <0.1%, <0.01%, <0.001%, or less).

In some embodiments, provided herein are KLC1C C-terminal peptide molecules that compete for binding with endogenous KLC1C. In some embodiments, provided herein are KLC1C C-terminal peptide molecules that comprise at least 70% sequence identity (e.g., 3 or fewer substitutions) with MRKMKLGLVN (SEQ ID NO: 1). In some embodiments, provided herein are peptide molecules that comprise at least 70% (e.g., 70%, 80%, 90%, 100%) sequence similarity (e.g., 3 or fewer non-conservative and/or semi-conservative substitutions) with MRKMKLGLVN (SEQ ID NO: 1). In some embodiments, the KLC1C C-terminal peptide is soluble. In some embodiments, the KLC1C C-terminal peptide is cell permeable. In some embodiments, the KLC1C C-terminal peptide is cell bioactive. In some embodiments, the KLC1C C-terminal peptide is cell permeable, enters endothelial cells, inhibits targeted recycling of the lateral border recycling compartment (LBRC), blocks transendothelial migration of tumor cells, and reduces/inhibits metastasis. In some embodiments, a C-terminal KLC1C peptide is conjugated to one or more functional moieties to impart desirable functionalities (e.g., solubility, bioavailability, cell-permeability) to the peptide. In some embodiments, a peptide/polypeptide functional moiety is conjugated to a C-terminal KLC1C peptide. In some embodiments, the C-terminal KLC1C peptide is conjugated to a cell-penetrating peptide (e.g., trans-activating transcriptional activator (TAT), antennapedia peptide, etc.).

In some embodiments, a KLC1C C-terminal peptide comprises:

```
                                         (SEQ ID NO: 3)
M(R/K)(R/K)M(R/K)(I/L/V/A)(G/A)(I/L/V/A)

(I/L/V/A)(N/Q);

(SEQ ID NO: 4)
M(R/K)(R/K)M(R/K)LGLVN;

(SEQ ID NO: 5)
MRKMK(I/L/V/A)G(I/L/V/A)(I/L/V/A)N;

(SEQ ID NO: 6)
M(R/K)(R/K)MKLGLV(N/Q);

(SEQ ID NO: 7)
MRKMK(I/L/V/A)G(I/L/V/A)(I/L/V/A)(N/Q);
``` or peptidomimetics thereof.

Some embodiments herein broadly relate to methods for the treatment or prevention of cancer and/or metastasis in a subject (e.g., a subject having or at risk of cancer and/or metastasis) comprising administering to the subject (or providing the subject with) an agent capable of inhibiting (e.g., attenuating the expression or activity of) kinesin-1, kinesin light chain (KLC), or kinesin light chain 1, variant 1 (KLC1C). In some embodiments, the inhibition of kinesin-1, KLC, or KLC1C reduces (e.g., inhibits) targeted recycling, TEM, migration of tumor cells across the endothelium, and/or metastasis. In some embodiments, a kinesin-1, KLC, or KLC1C inhibitor is selected from: (i) an oligonucleotide capable of attenuating the expression of kinesin-1, KLC, or KLC1C (e.g., small interfering RNA (siRNA), small hairpin RNA (shRNA), micro RNA (miRNA), a ribozyme, an antisense oligonucleotide, etc.); (ii) an anti-kinesin-1, anti-KLC, or anti-KLC1C antibody (or antibody fragment), peptide, or polypeptide capable of binding to kinesin-1, KLC, or KLC1C and inhibiting its activity; and a potent small molecule inhibitor of the activity of kinesin-1, KLC, or KLC1C.

In some embodiments, provided herein are pharmaceutical compositions comprising inhibitors of kinesin-1, KLC, and/or KLC1C (e.g., inhibitors of expression and/or activity). In some embodiments, provided herein are pharmaceutical compositions comprising inhibitors of KLC1C expression. In some embodiments, provided herein are pharmaceutical compositions comprising inhibitors of KLC1C cargo binding (e.g., small molecules, peptides, antibodies, etc.). In some embodiments, provided herein are pharmaceutical compositions comprising competitors of KLC1C cargo binding (e.g., synthetic C-terminal KLC1C peptides). Such pharmaceutical compositions comprise a therapeutically effective amount of the active agent and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals and more particularly in humans.

In some embodiments, provided herein are bioactive peptide molecules that inhibit KLC1C activity (e.g., inhibit the binding of KLC1C to its cargo). In some embodiments, a peptide inhibitor of KLC1C is provided. In some embodiments, the inhibitor binds to KLC1C (e.g., the C-terminal portion of KLC1C (e.g., SEQ ID NO: 1)) and prevents KLC1C from binding its cargo. In some embodiments, the inhibitor peptide is cell permeable. In some embodiments, the inhibitor peptide enters endothelial cells, prevents/inhibits binding of KLC1C to its cargo, inhibits targeted recycling of the lateral border recycling compartment (LBRC) block transendothelial migration of tumor cells, and reduces/inhibits metastasis. In some embodiments, an inhibitor peptide is conjugated to one or more functional moieties to impart desirable functionalities (e.g., solubility, bioavailability, cell-permeability) to the peptide. In some embodiments, a peptide/polypeptide functional moiety is conjugated to an inhibitor peptide. In some embodiments, the inhibitor peptide is conjugated to a cell-penetrating peptide (e.g., transactivating transcriptional activator (TAT), antennapedia peptide, etc.).

In some embodiments the technology provides antibodies or antibody fragments for inhibiting the binding activity of KLC1C to its cargo. In some embodiments, an antibody or antibody fragment recognizes the C-terminal region of KLC1C (e.g., SEQ ID NO: 1). In some embodiments, an antibody or antibody fragment recognizes an amino acid sequence comprising SEQ ID NO: 1. In some embodiments, an antibody or antibody fragment recognizes an amino acid sequence that is a portion of SEQ ID NO: 1. In some embodiments, an antibody or antibody fragment is specific for KLC1C and does not bind other kinesins or kinesin light chains. In some embodiments, an antibody or antibody fragment is specific for KLC1C binds other kinesins or kinesin light chains with lesser affinity than to KLC1C (e.g., <50%, <25%, <10%, <5%, <1%, <0.1%, <0.01%, <0.001%, or less). In some embodiments, an antibody is a neutralizing antibody. In some embodiments, KLC1C cannot bind its cargo when the antibody is bound.

In some embodiments, the antibody is a monoclonal antibody and in some embodiments the antibody is a polyclonal antibody. In some embodiments, the antibody is, for example, a human, humanized, or chimeric antibody. Monoclonal antibodies against target antigens are produced by a variety of techniques including conventional monoclonal antibody methodologies such as the somatic cell hybridization techniques of Köhler and Milstein (Nature, 256:495 (1975)). Although in some embodiments, somatic cell hybridization procedures are preferred, other techniques for producing monoclonal antibodies are contemplated as well (e.g., viral or oncogenic transformation of B lymphocytes).

Some embodiments the technology provide small molecule agents for inhibiting the binding activity of KLC1C to its cargo. In some embodiments, the small molecule agent binds to KLC1C (e.g., the c-terminus of KLC1C) and prevents KLC1C from binding its cargo (e.g., sterically, by inducing a conformational change, etc.). In some embodiments, the small molecule agent binds to the cargo of KLC1C and prevents KLC1C (e.g., the c-terminus of KLC1C) from binding its cargo (e.g., sterically, by inducing a conformational change, etc.). In some embodiments, a small molecule agent is soluble, cell permeable, biocompatible, etc.

In some embodiments, compositions and methods are provided to inhibit the expression of KLC1C. In some embodiments, a nucleic acid is used to modulate (e.g., inhibit) expression of KLC1C.

In some embodiments a small interfering RNA (siRNA) is designed to target and degrade a nucleic acid encoding KLC1C. siRNAs are double-stranded RNA molecules of 20-25 nucleotides in length. While not limited in their features, typically an siRNA is 21 nucleotides long and has 2-nt 3' overhangs on both ends. Each strand has a 5' phosphate group and a 3' hydroxyl group. In vivo, this structure is the result of processing by Dicer, an enzyme that converts either long dsRNAs or small hairpin RNAs (shRNAs) into siRNAs. However, siRNAs can also be synthesized and exogenously introduced into cells to bring about the specific knockdown of a gene of interest. Essentially any gene of which the sequence is known can be targeted based on sequence complementarity with an appropriately tailored siRNA. For example, those of ordinary skill in the art can synthesize an siRNA (see, e.g., Elbashir, et al., Nature 411:494 (2001); Elbashir, et al. Genes Dev 15:188 (2001); Tuschl T, et al., Genes Dev 13:3191 (1999)).

In some embodiments, RNAi is utilized to inhibit KLC1C. RNAi represents an evolutionarily conserved cellular defense for controlling the expression of foreign genes in most eukaryotes, including humans. RNAi is typically triggered by double-stranded RNA (dsRNA) and causes sequence-specific degradation of single-stranded target RNAs (e.g., an mRNA). The mediators of mRNA degradation are small interfering RNAs (siRNAs), which are normally produced from long dsRNA by enzymatic cleavage in the cell. siRNAs are generally approximately twenty-one nucleotides in length (e.g. 21-23 nucleotides in length) and have a base-paired structure characterized by two-nucleotide 3' overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, an RNase III enzyme (e.g., Dicer) converts the longer dsRNA into 21-23 nt double-stranded siRNA fragments. In some embodiments, RNAi oligonucleotides are designed to target KLC1C.

In other embodiments, shRNA techniques (See e.g., US 2008/0025958, herein incorporated by reference in its entirety) are utilized to modulate (e.g., inhibit) expression of KLC1C. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it. shRNA is transcribed by RNA polymerase III.

In some embodiments, the technology described herein uses antisense nucleic acid (e.g., an antisense DNA oligo, an antisense RNA oligo) to modulate (e.g., inhibit) the expression of KLC1C. For example, in some embodiments, expression modulated (e.g., inhibited) using antisense compounds that specifically hybridize with one or more nucleic acids encoding KLC1C. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of KLC1C.

In some embodiments, methods are provided for inhibiting TEM. In some embodiments, methods are provided for inhibiting targeted recycling of the LBRC. In some embodiments, methods are provided to prevent/reduce migration of tumor cells from the vasculature into tissues. In some embodiments, methods are provided to prevent/reduce metastasis. In some embodiments, such methods have no effect on adhesion of monocytes to the endothelial monolayers or migration of monocytes to the endothelial cell borders. In some embodiments, methods herein have no effect on constitutive recycling of the LBRC and only affects targeted recycling of the LBRC to the site of TEM.

In some embodiments, compositions and methods are provided for treating/preventing metastasis and diseases/conditions related thereto (e.g., metastatic cancer). In some embodiments, secondary cancers related to metastasis are inhibited/reduced. In some embodiments, compositions and methods herein relate to the prevention/reduction of metastasis (e.g., preventing/reducing transendothelial migration of tumor cells) from a primary cancer. Such primary cancers (e.g., primary tumor location) and/or tumor locations include, but are not limited to, the lung, bladder, ovary, rectum, stomach, thyroid, uterus, breast, skin (e.g., melanoma), colon, kidney, prostate, pancreas, liver, cervix, testicle, etc. In some embodiments, compositions and methods herein relate to the prevention/reduction of metastasis (e.g., preventing/reducing transendothelial migration of tumor cells) in tissues. Such tissues (e.g., secondary locations, sites of metastasis, etc.) for with migration to is prevented/reduced include, but are not limited to the bone, liver, lung, brain, peritoneum, adrenal gland, skin, muscle, vagina, etc. In some embodiments, compositions and methods herein prevent/reduce metastasis generally. In some embodiments, compositions and methods herein prevent/reduce one or more specific (and/or common) routes of metastasis. In some embodiments, compositions and methods herein prevent/reduce metastasis from one or more of the following, but not limited to these combinations: bladder to bone, liver, and/or lung; breast to bone, brain, liver, and/or lung; colon to liver, lung, and/or peritoneum; kidney to adrenal gland, bone, brain, liver, and/or lung; lung to adrenal gland, bone, brain, liver, and/or other lung; melanoma to bone, brain, liver, lung, skin, and/or muscle; ovary to liver, lung, and/or peritoneum; pancreas to liver, lung, and/or peritoneum; prostate to adrenal gland, bone, liver, and/or lung; rectum to liver, lung, and/or peritoneum; stomach to liver, lung, and/or peritoneum; thyroid to bone, liver, and/or lung; uterus to bone, liver, lung, peritoneum, and/or vagina.

There are at least 45 kinesin family heavy chains, some with associated cargo-binding light chains, and all associated with specific cargo-binding adapter molecules. They all have important functions in cell physiology. In some embodiments, by targeting one splice variant of one specific light chain of one specific kinesin (e.g., KLC1C) all other kinesin-1 light chain 1 functions and all other microtubule molecular motor functions are unaffected and/or minimally affected (e.g., <50%, <25%, <10%, <5%, <1%, <0.1%, <0.01%, <0.001%, or less).

In some embodiments, various peptide/polypeptides are employed in embodiments herein. In some embodiments, a peptide/polypeptide described herein (e.g., KLC1C C-terminal peptide, KLC1C inhibitor peptide, etc.) is artificial. In some embodiments, a peptide/polypeptide described herein (e.g., KLC1C C-terminal peptide, KLC1C inhibitor peptide, etc.) is prepared by methods known to those of ordinary skill in the art. For example, the peptide can be synthesized using solid phase polypeptide synthesis techniques (e.g. Fmoc or Boc chemistry). Alternatively, the peptide can be produced using recombinant DNA technology (e.g., using bacterial or eukaryotic expression systems). Further, a peptide or polypeptide may be expressed within a subject (e.g., following administration of an appropriate vector). Accordingly, to facilitate such methods, provided herein are genetic vectors (e.g., plasmids, viral vectors (e.g. AAV), etc.) comprising a sequence encoding the peptide, as well as host cells comprising such vectors. Furthermore, provided herein are the peptides and polypeptides produced via such methods.

Embodiments are not limited to the specific peptide/polypeptide sequences listed herein. In some embodiments, peptides/polypeptides meeting limitations described herein and having substitutions not explicitly described are within the scope of embodiments here. In some embodiments, the peptides/polypeptides described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides/polypeptides described herein may be modified by conservative residue substitutions, for example, of the charged residues (K to R, R to K, D to E and E to D). Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, any embodiments described herein may comprise mimetics corresponding to all or a portion of the peptides/polypeptides described herein (e.g., KLC1C C-terminal peptide, KLC1C inhibitor peptide, etc.), with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, 8-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N (G)-nitroarginine), nitrosoarginine (N(G)-nitrosoarginine), methylarginine (N-methyl-arginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methyl-histidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methyl-serine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the peptide/polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46, 47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methylencamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, the peptide/polypeptide described herein (e.g., KLC1C C-terminal peptide, KLC1C inhibitor peptide, etc.) are provided as fusions with other peptides or polypeptides. Such fusions may be expressed from a recombinant DNA which encodes the peptide/polypeptide described herein (e.g., KLC1C C-terminal peptide, KLC1C inhibitor peptide, etc.) and the additional peptide/polypeptide or may be formed by chemical synthesis. For instance, the fusion may comprise a cell-penetrating peptide (e.g., trans-activating transcriptional activator (TAT), antennapedia peptide, etc.), an enzyme of interest, a luciferase, RNasin or RNase, and/or a channel protein (e.g., ion channel protein), a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein, a targeting sequence (e.g., a myristylation sequence), a mitochondrial localization sequence, or a nuclear localization sequence. The functional peptide/polypeptide may be fused to the N-terminus and/or the C-terminus of the peptide/polypeptide described herein (e.g., KLC1C C-terminal peptide, KLC1C inhibitor peptide, etc.). In one embodiment, the fusion protein comprises a first peptide/polypeptide at the N-terminus and another (different) peptide/polypeptide at the C-terminus of the peptide/polypeptide described herein (e.g., KLC1C C-terminal peptide, KLC1C inhibitor peptide, etc.). Optionally, the elements in the fusion are separated by a connector sequence, e.g., preferably one having at least 2 amino acid residues, such as one having 13 and up to 40 or 50 amino acid residues. The presence of a connector sequence in a fusion protein of the invention does not substantially alter the function of either element in the fusion relative to the function of each individual element, likely due to the connector sequence providing flexibility (autonomy) for each element in the fusion. In certain embodiment, the connector sequence is a sequence recognized by an enzyme or is photocleavable. For example, the connector sequence may include a protease recognition site.

In some embodiments, provided herein are pharmaceutical compositions comprising of one or more peptide/polypeptide described herein (e.g., KLC1C C-terminal peptide, KLC1C inhibitor peptide, etc.) and a pharmaceutically acceptable carrier. Any carrier which can supply an active peptide or polypeptide (e.g., without destroying the peptide or polypeptide within the carrier) is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intrasternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), etc.

Various delivery systems are known and may be used in certain embodiments to administer an inhibitor described herein (e.g. encapsulation in liposomes, microparticles, microcapsules, etc.). Methods of introduction include but are not limited to intradermal, intramuscular, intraperitoneal, intratumoral, intravenous, subcutaneous, intranasal, epidural, and oral routes. In some embodiments, inhibitors are administered by any convenient route, for example by infusion or bolus injection, by absorption through epithelial or mucocutaneous linings (e.g., oral mucosa, rectal and intestinal mucosa, etc.) and may be administered together with other biologically active agents (e.g., sequentially, simultaneously, separately-formulated, co-formulated, etc.). Administration may be systemic or local. In some embodiments, it is desirable to introduce the inhibitors into the circulation system by any suitable route. Pulmonary administration may also be employed (e.g., by use of an inhaler or nebulizer, and formulation with an acrosolizing agent).

In some embodiments, inhibitors are administered locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

"Effective amount" refers to the amount or dose of the inhibitor, upon single or multiple dose administration to the patient, which provides the desired effect in the patient under treatment. An effective amount can be readily determined by the attending diagnostician, as one skilled in the art, by the use of known techniques and by observing results obtained under analogous circumstances. In determining the effective amount or dose of agent administered, a number of factors are considered by the attending diagnostician, including, but not limited to: the species of mammal; its size, age, and general health; the specific disease involved; the degree of or involvement or the severity of the disease; the response of the individual patient; the particular inhibitor administered; the mode of administration; the bioavailabilty characteristics of the preparation administered; the dose regimen selected; the use of concomitant medication; and other relevant circumstances.

The term "carrier" refers to a diluent, adjuvant, excipient, or vehicle with which the compound or pro-drug of the invention is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol and water. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

Typically, compositions for intravenous administration are solutions in sterile isotonic aqueous buffer. Where necessary, the composition may also include a solubilizing agent and a local anesthetic such as lignocaine to, case pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

In various embodiments, the bioactive agent (e.g., peptide, antibody, small molecule, etc.) is administered in an amount, on a schedule, and for a duration sufficient to decrease triglyceride levels by at least 5%, 10%, 15%, 20% or 25% or more as compared to levels just prior to initiation of treatment. In some embodiments, the bioactive agent is administered in an amount, on a dosage schedule, and for a duration sufficient to decrease oxalate levels (e.g., in urine, in plasma) by at least 10%, 15%, 20%, 25%, 30%, 35%, 40%, 45% or 50%. In particular embodiments, the bioactive agent is administered in an amount, on a schedule, and for a time sufficient to decrease oxalate levels (e.g., in urine, in plasma) by at least 55%, 60%, 65%, even at least about 70% or more.

In certain embodiments, the bioactive agent (e.g., peptide, antibody, small molecule, etc.) is administered in an amount, expressed as a daily equivalent dose regardless of dosing frequency, of 50 micrograms ("mcg") per day, 60 mcg per day, 70 mcg per day, 75 meg per day, 100 mcg per day, 150 mcg per day, 200 meg per day, or 250 mcg per day. In some embodiments, the bioactive agent is administered in an amount of 500 mcg per day, 750 mcg per day, or 1 milligram ("mg") per day. In yet further embodiments, the bioactive agent is administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day.

In various embodiments, a bioactive agent (e.g., peptide, antibody, small molecule, etc.) is administered on a monthly dosage schedule. In other embodiments, the bioactive agent is administered biweekly. In yet other embodiments, the bioactive agent is administered weekly. In certain embodiments, the bioactive agent is administered daily ("QD"). In select embodiments, the bioactive agent is administered twice a day ("BID").

In typical embodiments, a bioactive agent (e.g., peptide, antibody, small molecule, etc.) is administered for at least 3 months, at least 6 months, at least 12 months, or more. In some embodiments, the bioactive agent is administered for at least 18 months, 2 years, 3 years, or more.

In some embodiments, methods and compositions are provided for co-administration of a bioactive agent (e.g., peptide, antibody, small molecule, etc.) with one or more additional pharmaceutical agents. In some embodiments, a subject is treated with (i) a composition comprising one of the bioactive agents described herein (e.g., KLC1c peptide, inhibitor of KLC1c expression or activity, etc.), as well as (ii) one or more treatments for cancer and/or metastasis. In some embodiments, an additional therapy for co-administration with the compositions herein is a cancer therapy. Such therapies include chemotherapy, immunotherapy, radiation, surgery, etc. In some embodiments, exemplary anticancer agents suitable for use in compositions and methods described herein include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MY-LERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurca, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and/or immunotherapeutics (e.g., checkpoint inhibitor).

EXPERIMENTAL

Example 1

Melanoma Cells can Transmigrate Via the LBRC In Vitro.

Figure 6:
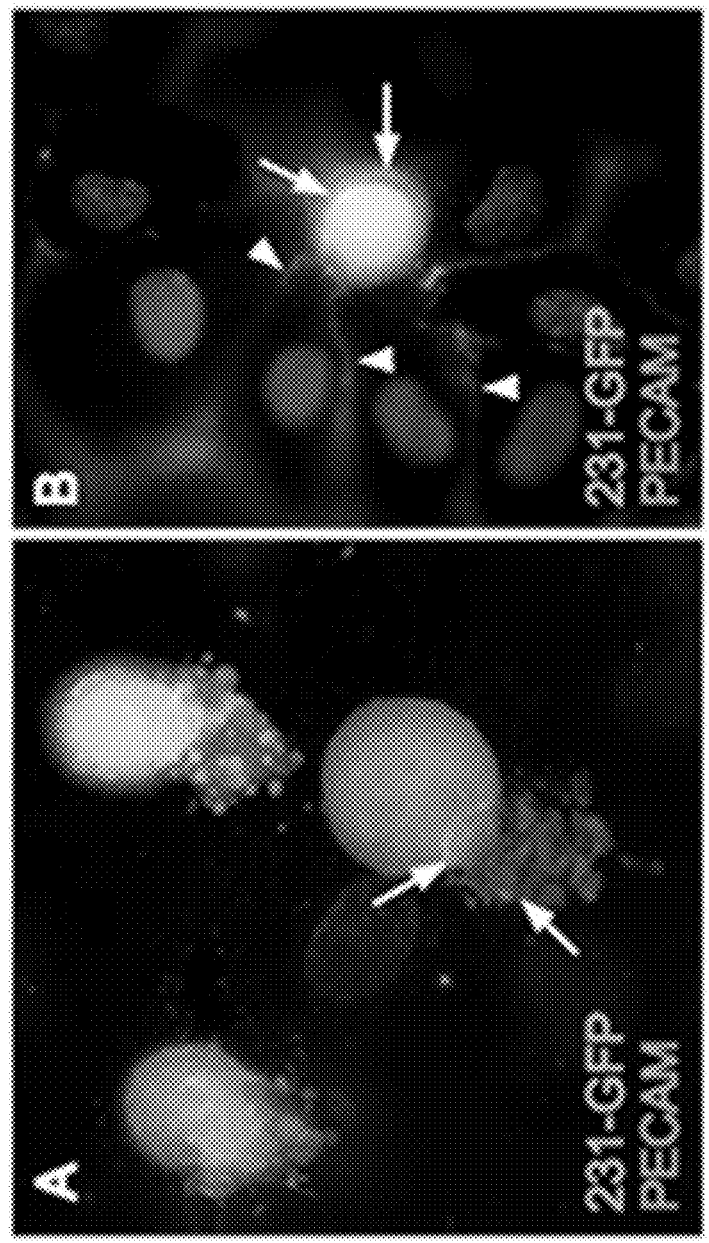
FIG. 6. Transmigrating tumor cells recruit the LBRC. GFP-labeled breast cancer cells (MDA-MB-231) caught in the act of transmigration of an EC monolayer. (A) Ring of PECAM as a surrogate marker of the LBRC is enriched around portion of cancer cell in the act of migration (arrows). (B) Brightness enhanced in another field to show that endothelial junctions are intact (arrowheads) in the vicinity of a transmigrating tumor cell. Enhanced PECAM staining (arrows) where LBRC abuts it.
Figure 7:
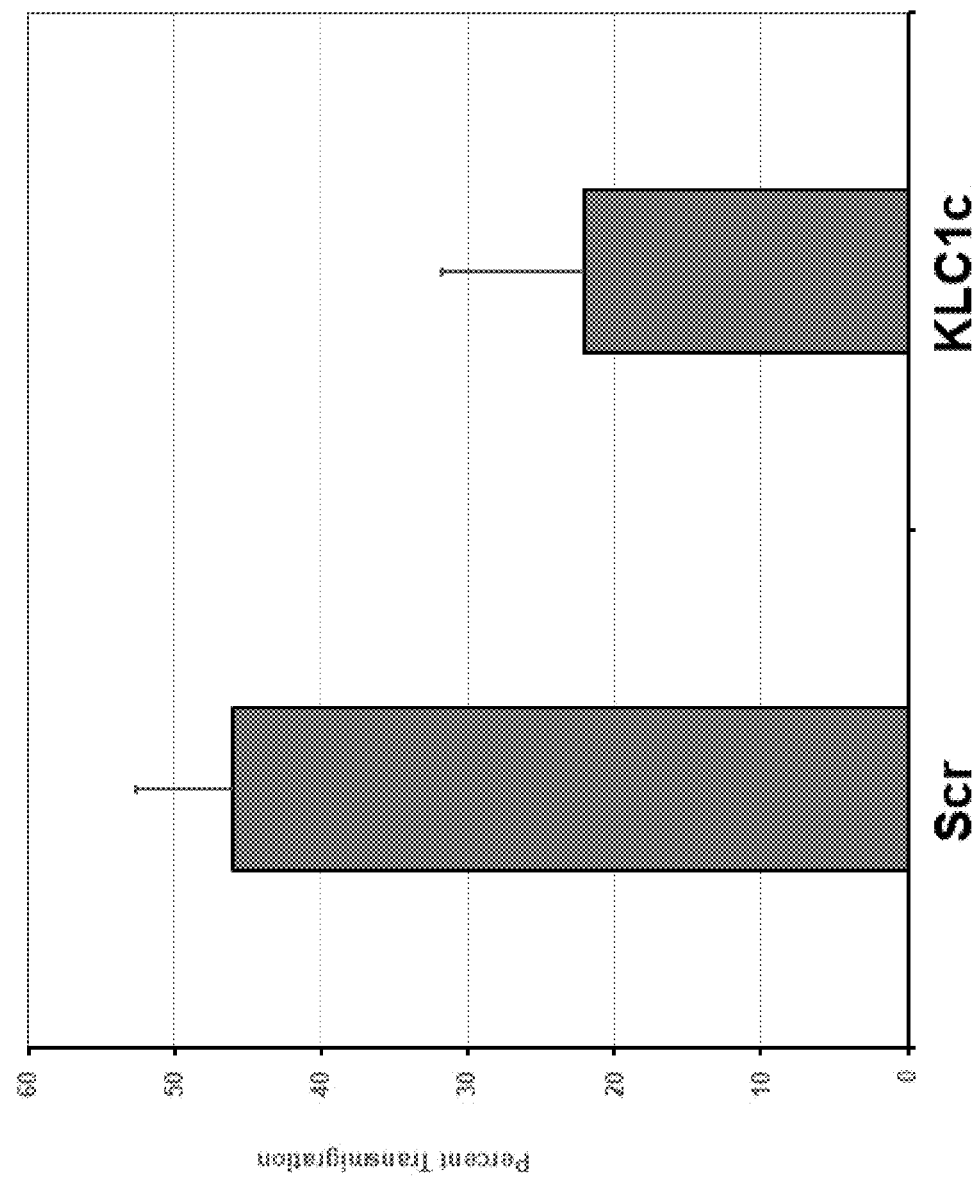
FIG. 7. Tat-KLC1c peptide blocks tumor cell TEM. A375 human melanoma cells were allowed to transmigrate for 2 hours across EC monolayers pre-incubated (then washed extensively) with Tat-KLC1c or Tat-Scr. The 50% block in TEM is representative of at least 6 independent experiments.
Figure 8:
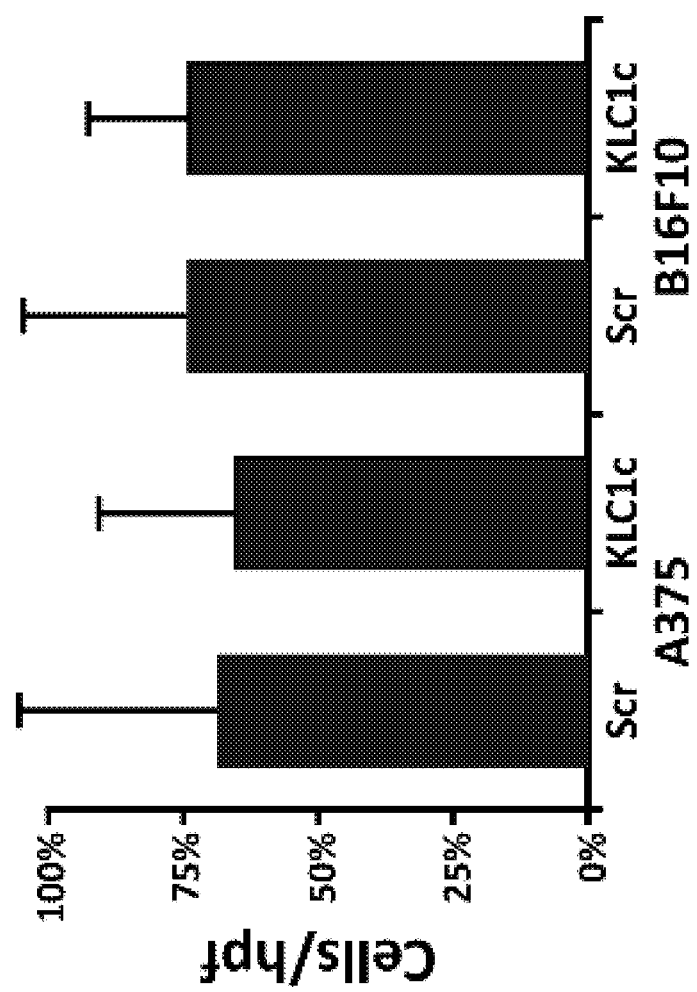
FIG. 8. Tat-KLC1c peptide has no direct effect on tumor cell migration. $1 \times 10^4$ A375 human melanoma cells or $1 \times 10^4$ B16F10 melanoma cells were resuspended in serum-free medium and placed in the upper chamber of Transwell filters (8 µM pore size) and allowed to migrate in response to serum-containing medium in the bottom chamber in the presence of 100 nM Tat-Scr, Tat-KLC1c or no additives. The total number of tumor cells in the bottom well 12 hours later was enumerated. Data are mean±S.D. for four replicates of each sample. There were no significant differences among the groups.
Figure 9:
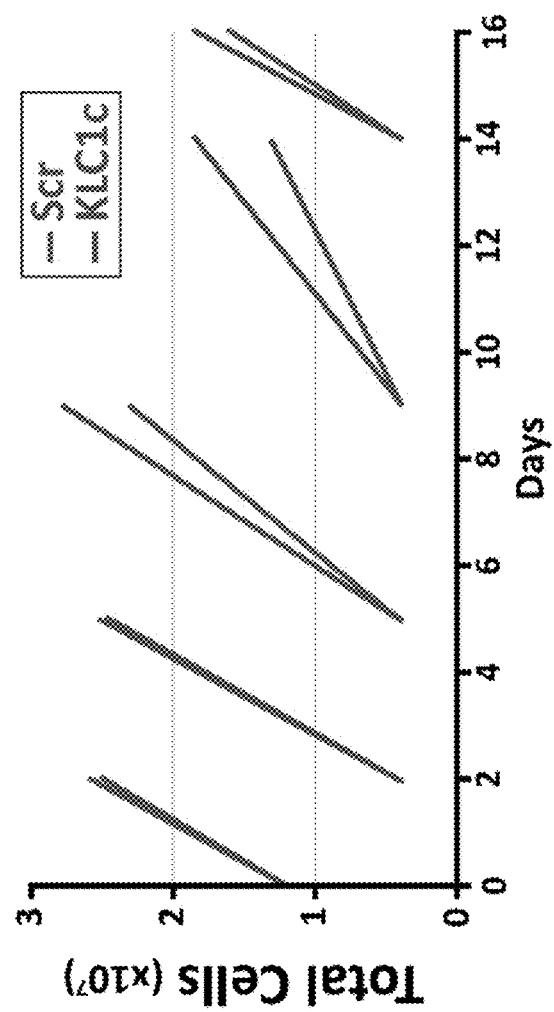
FIG. 9. Tat-KLC1c peptide does not affect growth of B16F10 melanoma cells over a two-week period. Melanoma cells were plated at a density of $1 \times 10^5$/ml on 80 mm plates with 100 nM Tat-Scr or Tat-KLC1c. Cells were trypsinized and counted on the indicated days, diluted and $4 \times 10^6$ viable cells re-plated in fresh peptide. Total cells in the culture are shown.

Using an in vitro assay that has been consistently validated over 25 years for leukocyte transmigration (Refs. B18, B19; herein incorporated by reference in their entireties), experiments conducted during development of embodiments herein demonstrated that a subset of human melanoma cells transmigrating a human EC monolayer do so by recruiting the LBRC (FIG. 6). Tumor cells that transmigrate using the LBRC do so without destroying the endothelial cell monolayer. Furthermore, the Tat-KLC1c peptide that blocks LBRC recruitment significantly blocks melanoma cell TEM in vitro, while the scrambled peptide has no effect (FIG. 7). The Tat-KLC1c peptide has no effect on the ability of tumor cells to move per se (FIG. 8), nor on tumor cell viability or growth (FIG. 9).

Figure 10:
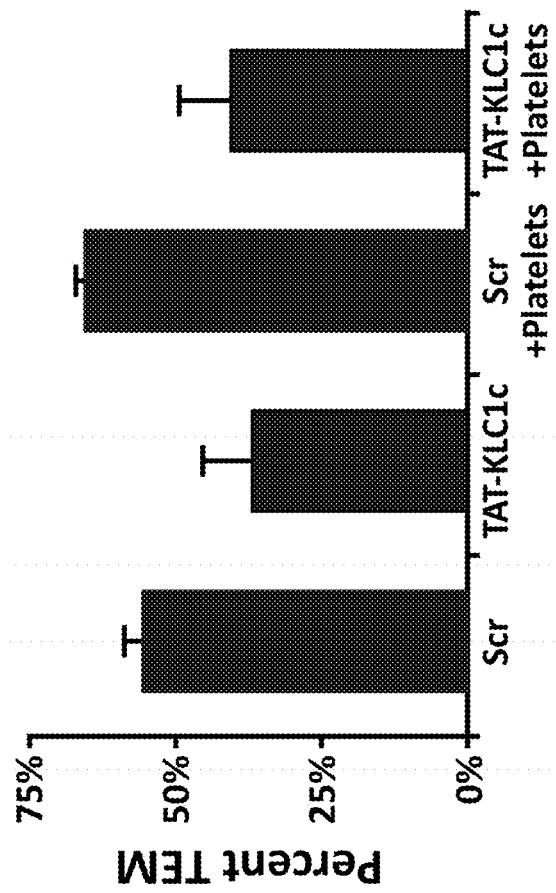
FIG. 10. Platelets modestly increase melanoma cell migration through an LBRC-dependent mechanism. The tumor cell TEM assay was carried out in the presence or absence of human platelets, which were added to the tumor cells at the time of peptide addition and immediately prior to addition to the endothelial cell monolayer. Transmigration proceeded for 2 hours. Addition of platelets to control monolayers (Scrm+Platelets) significantly enhanced A375 melanoma TEM ($p<0.05$ vs. Scr). Tat-KLC1c peptide reduced tumor cell TEM by 33% (*$p<0.0001$ vs. scr) and also reduced the additional TEM in the presence of platelets down to the same level (Tat-KLC1c vs. Tat-KLC1c+ Platelets=N.S.)

Experiments conducted during development of embodiments herein found no significant effect of peripheral blood mononuclear cells on transmigration efficiency. The addition of platelets did enhance transmigration efficiency and the increased transmigration was also blocked by the Tat-KLC1c peptide, indicating that the additional transmigration in the presence of platelets was mediated by recruiting the LBRC (FIG. 10). Among other things, activated platelets secrete both ROS and $PGE_2$, which could contribute to LBRC recruitment (See FIGS. 17-19).

Example 2

Tat-KLC1c Peptide Blocks Tumor Cell Transmigration In Vivo

Figure 11:
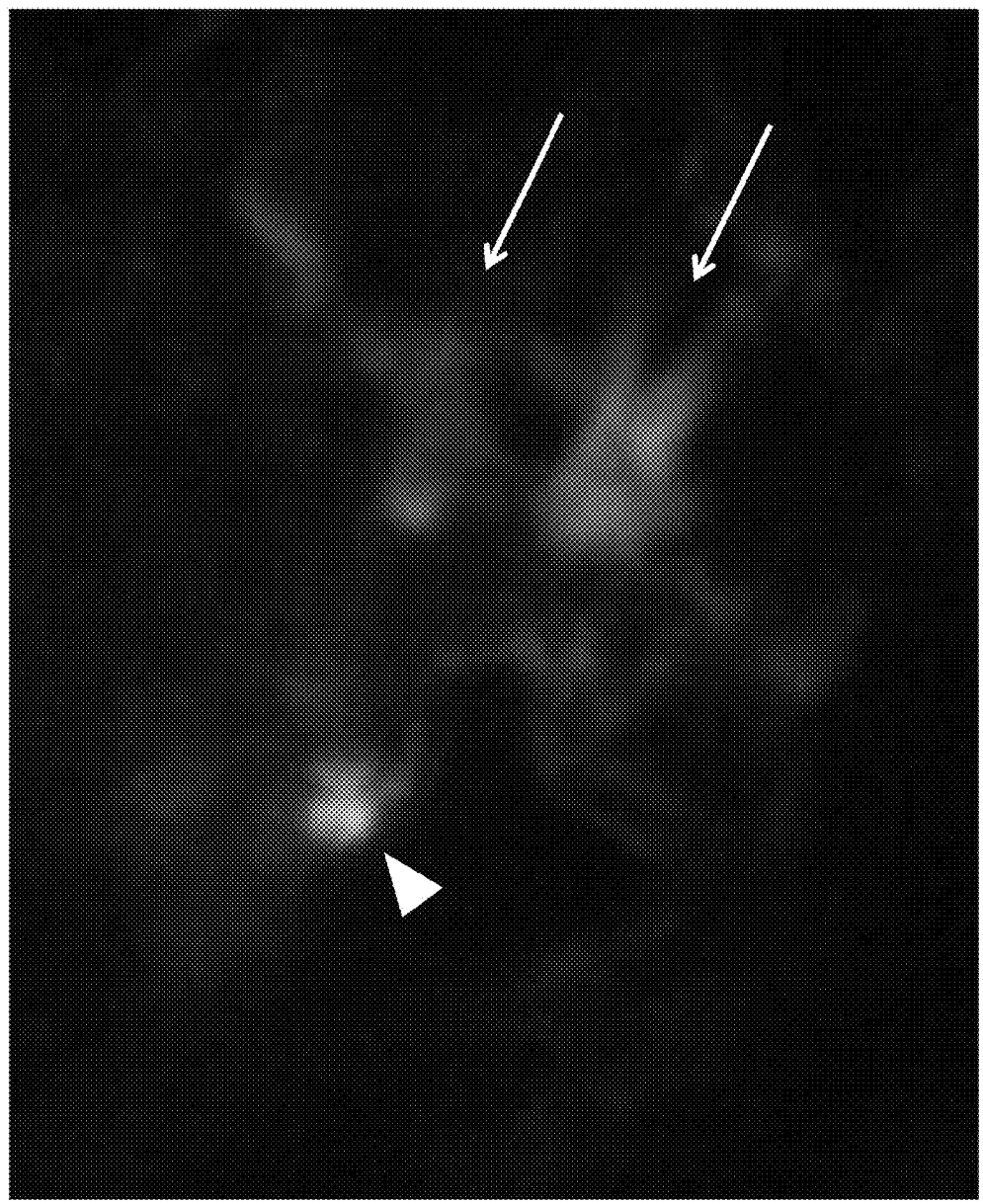
FIG. 11. Visualizing melanoma cell extravasation in vivo. Single XY plane from confocal image of CFSE-labeled B16F10 cells in Tat-Ser treated mouse lung 6 hr. after i.v. injection of $10^6$ tumor cells. Two tumor cells (arrows) have migrated out of vasculature while another one (arrowhead) remains inside the vessel.
Figure 12:
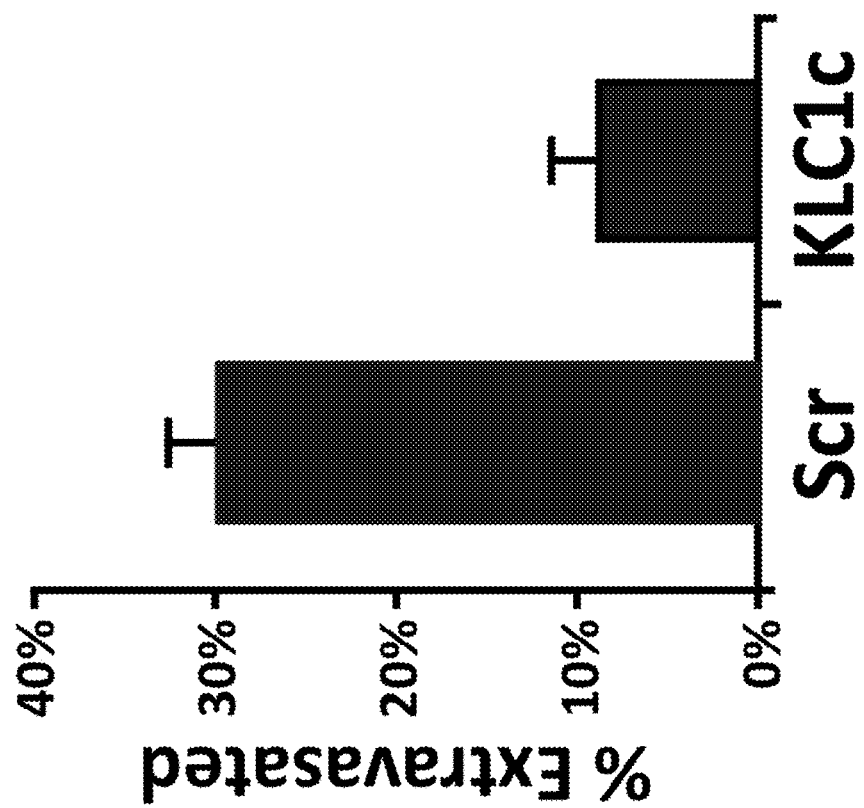
FIG. 12. Tat-KLC1c blocks melanoma extravasation. Quantification of block by Tat-KLC1c (Mean±S.D) *$p<0.01$.
Figure 13A:
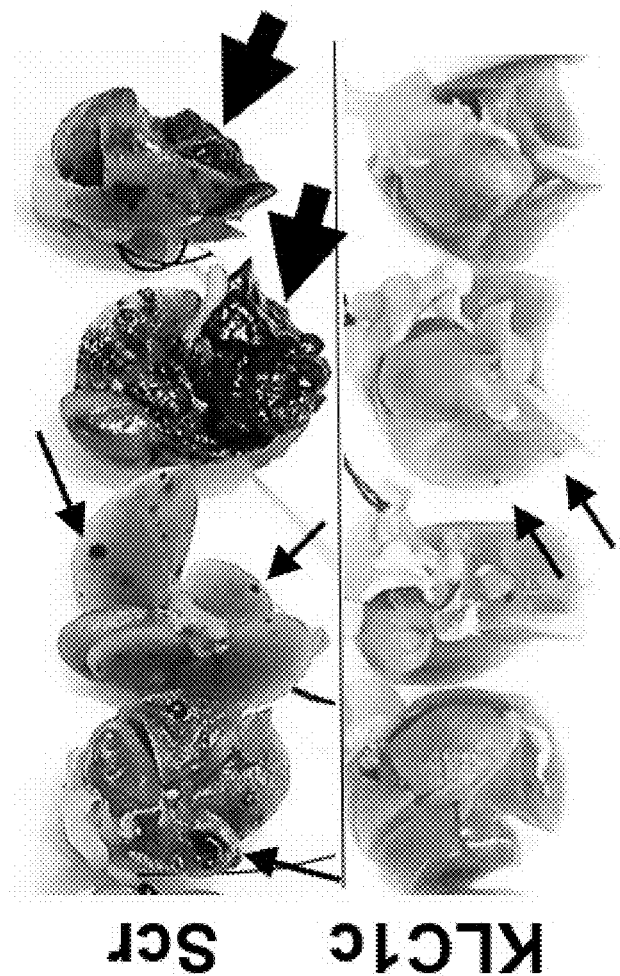
FIG. 13A-B. Tat-KLC1c treatment prevents metastatic colony formation. Age- and sex-matched C57Bl/6 mice were injected with Tat-Scr (Scr) or Tat-KLC1c (KLC1c) 1 hr before and 18 hr after injection of $10^6$ B16F10 melanoma cells via tail vein. 14 days later lungs were inflated with formalin, and metastases counted. (A) Representative gross photos of lungs from mice that received Tat-Scr (top) and Tat-KLC1c (bottom). Arrows point to some of the metastases. (B) Graphical representation of results. Dots are values for individual mice. (TNTC)=too numerous to count. Lines show mean±S.D., p=0.00204 by ANOVA not including the TNTC data.
Figure 13B:
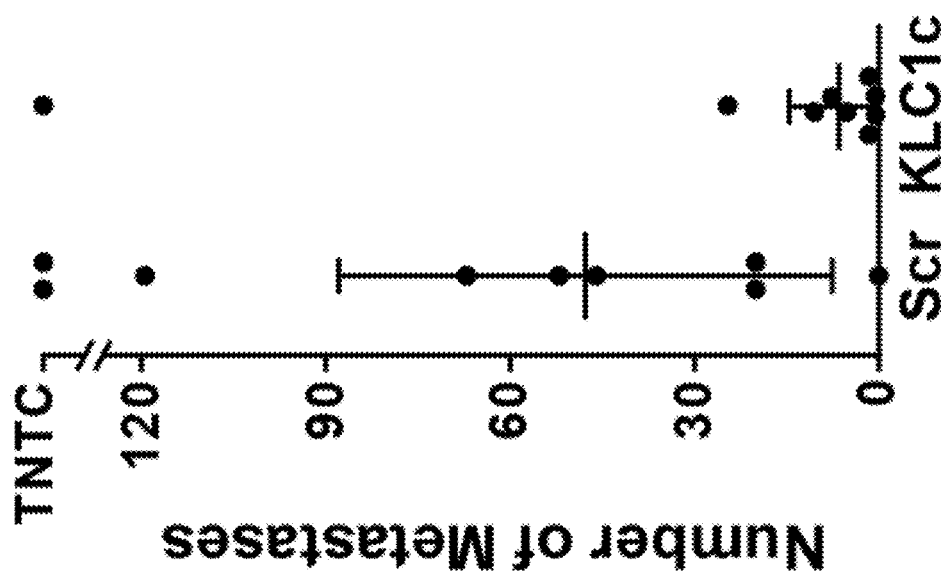

C57Bl/6 mice received KLC1c or scrambled peptide 1 hour prior to receiving carboxyfluorescein (CFSE)-labeled B16F10 melanoma cells via tail vein. They were sacrificed six hours later so that data would reflect the effects on extravasation per se rather than survival or growth (Ref. B10; herein incorporated by reference in its entirety). Immediately prior to sacrifice a fluorescent anti-PECAM antibody was injected i.v. to stain vasculature. Lungs were inflated with 4% paraformaldehyde (PFA) and fixed overnight in PFA, then cryopreserved in sucrose. 100 µm thick frozen sections were cut and examined by spinning disc confocal microscopy with images taken every 1 µm of specimen depth. 30% of visualized tumor cells had transmigrated in the mice receiving scrambled peptide, whereas only ~9% had transmigrated in mice receiving Tat-KLC1c peptide—a 70% reduction (FIGS. 11,12). The Tat-KLC1c peptide significantly blocked the establishment of metastatic colonies. In a separate experiment, age- and sex-matched C57Bl/6 mice syngeneic to the tumor were randomized to receive Tat-Ser or Tat-KLC1c parenterally at a concentration calculated to achieve 0.1 µM in vivo 1 h. before and 18 h. after receiving $1 \times 10^6$ syngeneic B16F10 melanoma cells in 100 µl via tail vein. Lung metastases were enumerated 14 days later under a dissecting microscope. The Tat-KLC1c group had over 90% fewer (FIG. 13, p=0.00204). An independent experiment using different lots of peptides corroborated these results (not shown). Even though Tat-KLC1c blocks about ⅓ (in vitro) to ⅔ (in vivo) of melanoma extravasation events, the number of metastatic colonies that grow out are disproportionately lower. This indicates that those melanoma cells that use the LBRC have some survival advantage.

Example 3

Figure 14:
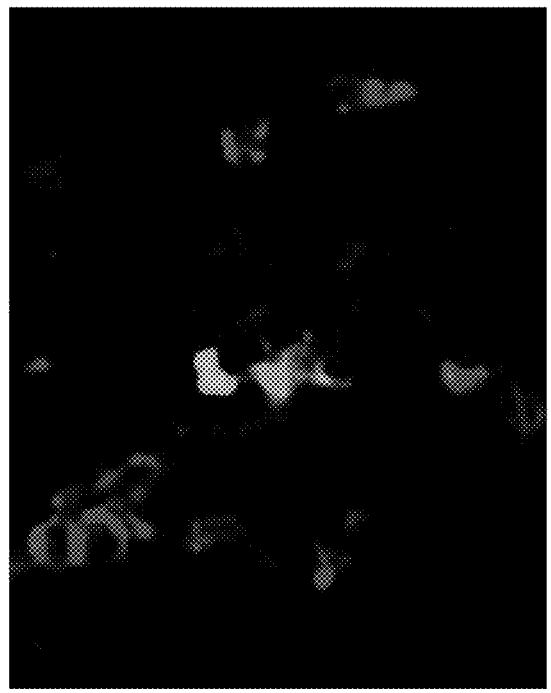
Figure 15:
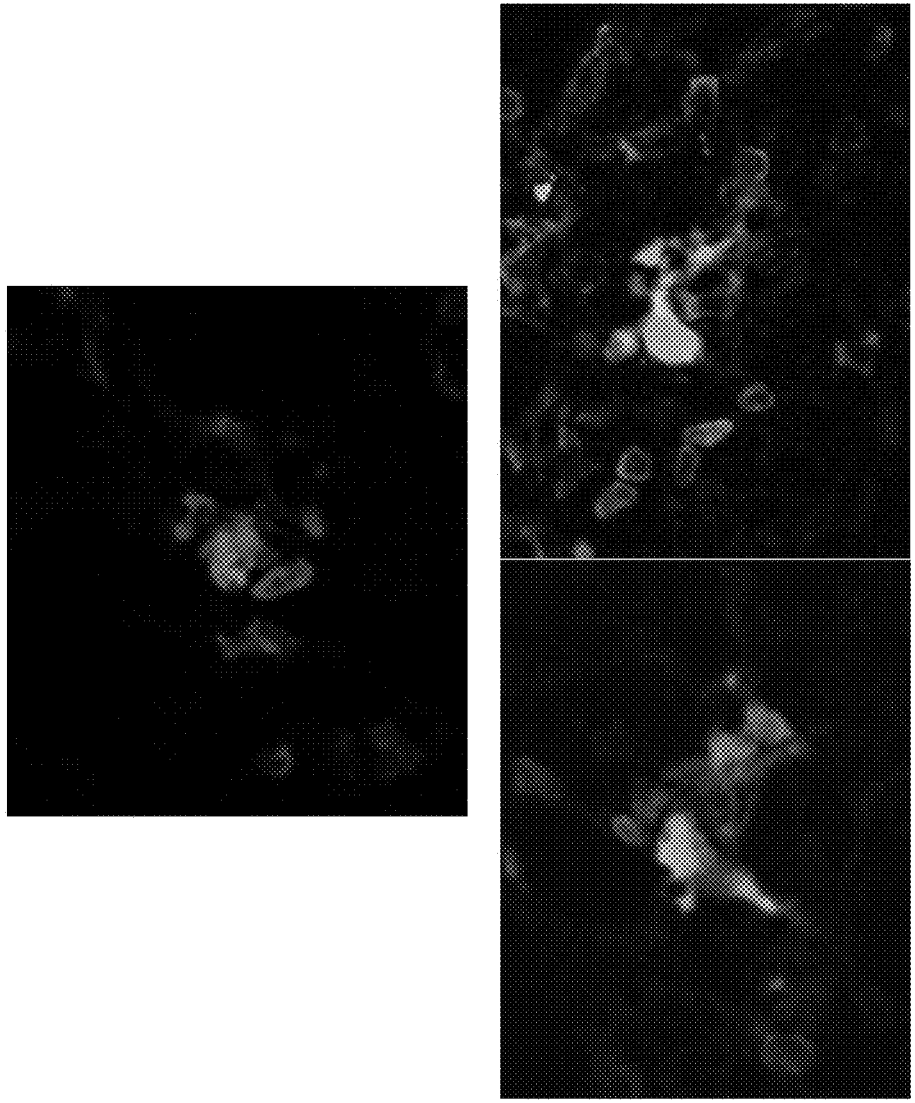
FIG. 15. B16F10 cells within lung parenchyma engaged with leukocytes. 96% of the tumor cells in mice pretreated with Tat-KLC1c but only 75% in mice treated with Tat-Scr were surrounded by leukocytes.

Determining Characteristics that Provide a Survival Advantage to Melanoma Cells that Use the LBRC to Extravasate Experiments are conducted during development of embodiments herein to examine recently-emigrated melanoma cells and quantify the inflammatory response they generate, the expression of putative melanoma stem cell markers, and the degree of tumor cell and inflammatory cell apoptosis. Experiments are conducted as in Example 2, but mice are sacrificed at appropriate times to examine the host response to the tumor cell extravasation. Early inflammatory response should manifest by day 2 and mature over the next few days. Tumor cells are labeled with carboxyfluorescein (CFSE) to facilitate locating them in lung tissue. Thick (100 µm) frozen sections are cut from the fixed and cryoprotected tissue to allow observation of the 3-dimensional relationship of tumors to the host tissue. Sections are fixed and gently permeabilized (0.3% Triton X-100 in PBS+2.5% BSA) to allow penetration of antibodies, then stained for markers of macrophages (F4/80), neutrophils (GR-1 or S100A9), monocytes (CD14), natural killer cells (CD56), or T cells (CD3). Selective staining for endothelial cells (CD31 or VE-cadherin) delineates intravascular vs. extravascular leukocytes. Additionally, samples are stained for markers of murine myeloid-derived suppressor cells (Arginase-1 and STAT-3) and Regulatory T cells (Tregs; Foxp3). Serial sections are also cut thin (5-10 µm) to allow detailed analysis of the leukocyte types involved in the inflammatory response as a function of time. Cleaved caspase 3 serve as a marker for apoptosis in either tumor cells or leukocytes. Experiments conducted during development of embodiments herein show that CFSE-labeled tumor cells are detected in lung tissue for at least 5 days (FIG. 14,15) and that 96% of those in mice treated with Tat-KLC1c, but only 75% of those treated with Tat-Scr provoked an inflammatory response (FIG. 15). This is consistent with the determination that melanoma cells that extravasate via the LBRC avoid stimulating an inflammatory response.

Example 4

Determining a Mechanism by which Circulating Melanoma Cells Recruit the LBRC

Heterophilic ligands for human PECAM have been reported, and at least one (paired immunoglobulin like receptor) has been reported for mouse CD99. Tumor cells could express heterophilic ligands to interact with these molecules on endothelial cells and recruit the LBRC. However, blocking antibodies against PECAM or CD99 would reduce tumor cell TEM.

Figure 16:
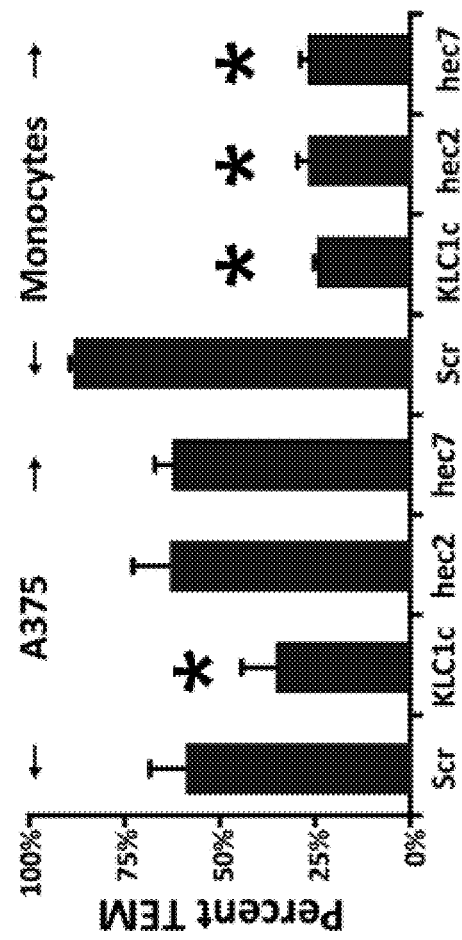
FIG. 16. A375M melanoma cells do not use heterophilic ligands for PECAM or CD99 to transmigrate. Anti-PECAM (hec7) and anti-CD99 (hec2) mAb blocked TEM of monocytes but not melanoma. Data are mean±SD of 6 replicates. *$p<0.005$ vs. Scr.

However, the A375M melanoma cell line that transmigrates so efficiently is not blocked by these antibodies (FIG. 16), indicating that these tumor cells recruit the LBRC my another mechanism.

Endothelial PECAM and CD99 signal through the cation channel TRPC6 and Protein Kinase A, respectively. Blocking PECAM or CD99 function blocks transmigration. However, this block is overcome by bypassing PECAM or CD99 by directly activating TRPC6 and PKA, respectively, when leukocytes are poised to transmigrate. Highly activated leukocytes can do the same. Tumor cells recruit the LBRC by sending alternative signals to the endothelial cell that activate the signaling pathways normally used by leukocytes (e.g., calcium flux or PKA activation) to promote recruitment of the LBRC. Experiments are conducted during development of embodiments herein to identify the signaling pathways for PECAM and CD99.

Figure 17:
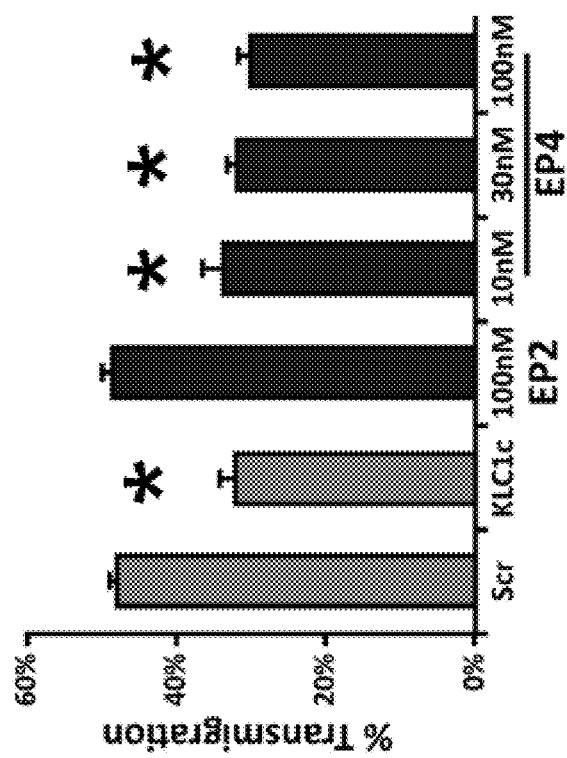
FIG. 17. EP4 inhibitor blocks melanoma transmigration. HUVEC monolayers were pretreated with 100 nM Tat peptides or the indicated doses of PF-04418948 (EP2 inhibitor) or AAT008 (EP4 antagonist) for 1 hour then washed exten-sively before adding A375 cells. Transmigration proceeded for 2 hours. Data show mean±S.D. of ≥3 replicates for each condition. *$p<0.01$.
Figure 18:
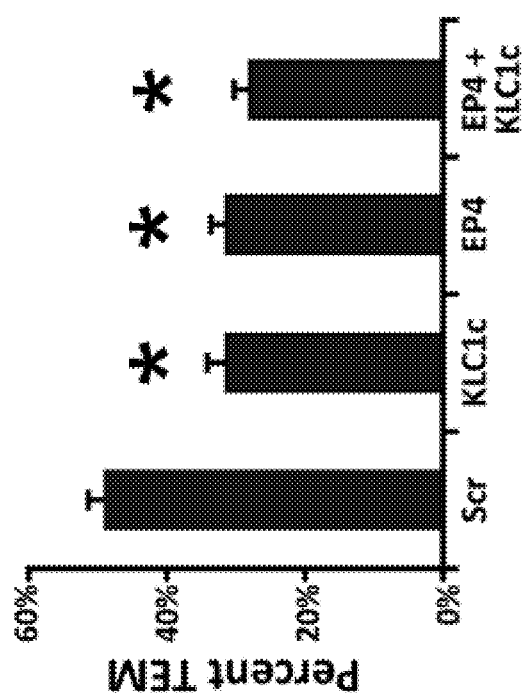
FIG. 18. Optimal concentrations of Tat-KLC1c peptide and EP4 antagonist are not additive. Transmigration assays as in FIG. 16 with 100 µM Tat-peptides, 100 nM AAT-008, or both. Mean±S.D. of 6 replicates for each condition. *$p<0.0004$ vs. Scr; NS vs each other.

Prostaglandin $E_2$ ($PGE_2$) activation of PKA overcomes a block to endothelial CD99 and recruit the LBRC to promote transmigration. Similarly, activation of PKA through the histamine H2 receptor has the same effect. Endothelial cells express all four $PGE_2$ receptors (EP1-EP4). There are specific inhibitors for each one that are effective at nM concentrations. In Experiments conducted during development of embodiments herein, specific inhibitors of each prostaglandin receptor used at 10× its $IC_{50}$ were able to block melanoma cell transmigration across endothelial cell monolayers using a specific inhibitor of EP4, AAT-008, while inhibitors of EP1, EP2, and EP3 had no effect (FIG. 17). EP2 and EP4 signal through Gas to stimulate adenylate cyclase for the activation of PKA. Inhibiting EP4 but not EP2 was effective, showing specificity. The block to melanoma cell transmigration was as effective as using Tat-KLC1c at its optimal concentration (FIG. 17,18). The combination of Tat-KLC1c and AAT-008 did not block any better than either one alone, indicating that the EP4 antagonist and Tat-KLC1c are acting on the same pathway (FIG. 18).

Figure 19:
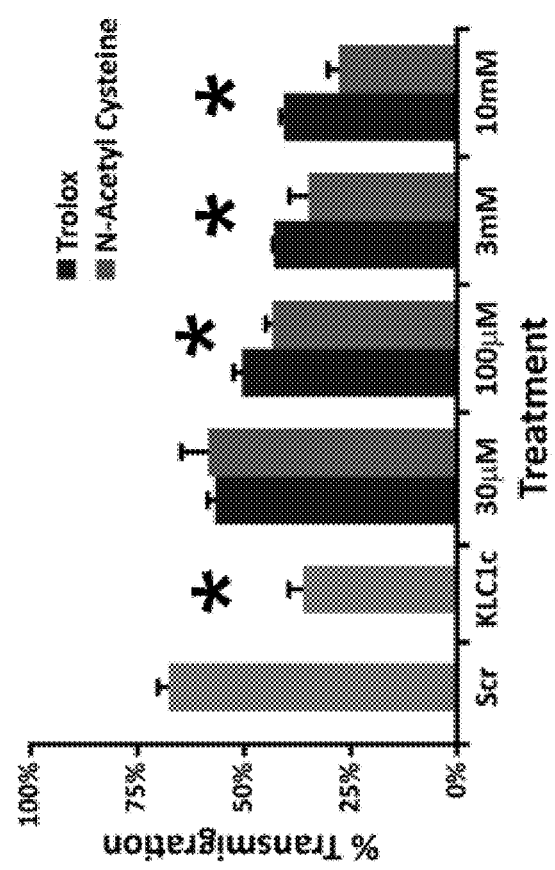
FIG. 19. Free radical scavengers and anti-oxidants inhibit melanoma transmigration. A375M transendothelial migration assays were carried out in the presence of Tat-peptides or the indicated concentrations of Trolox or N-acetylcysteine. Data are mean±SD of ≥3 replicates for each condition. *$p<0.01$ for all inhibitors vs. Scr.

Under certain conditions, reactive oxygen species (ROS) produced by neutrophils can activate calcium influx into endothelial cells via the endothelial cell TRPM2 channel. This calcium flux promotes transendothelial migration of the neutrophils. Experiments are conducted during development of embodiments herein to demonstrate ROS produced by tumor cells can activate endothelial cell calcium flux, possibly via TRPM2, bypassing the need for PECAM-induced calcium flux via TRPC6. Experiments conducted during development of embodiments herein demonstrate that the free radical scavenger and anti-oxidant compounds 6-hydroxy-2,5,7,8-tetramethylchroman-2-carboxylic acid (Trolox) and N-acetylcysteine reduces tumor cell transmigration in a dose-dependent manner with significant effects at concentrations as low as 100 μM. At 10 mM, they inhibit melanoma cell TEM as effectively as the optimal concentration of Tat-KLC1c peptide (FIG. 19).

All publications and patents mentioned herein are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above by number, are herein incorporated by reference in their entireties.

[A1] Butcher E C: Leukocyte-endothelial cell recognition: three (or more) steps to specificity and diversity. Cell 1991, 67:1033-6.

[A2] Ley K, Laudanna C, Cybulsky M I, Nourshargh S: Getting to the site of inflammation: the leukocyte adhesion cascade updated. Nat Rev Immunol 2007, 7:678-89.

[A3] Muller W A: Mechanisms of leukocyte transendothelial migration. Annu Rev Pathol 2011, 6:323-44.

[A4] Zen K, Parkos, C. A.: Leukocyte-epithelial interactions. Curr Opin Cell Biol 2003, 15:557-64.

[A5] Mamdouh Z, Chen X, Pierini L M, Maxfield F R, Muller W A: Targeted recycling of PECAM from endothelial cell surface-connected compartments during diapedesis. Nature 2003, 421:748-53.

[A6] Mamdouh Z, Kreitzer G E, Muller W A: Leukocyte transmigration requires kinesin-mediated microtubule-dependent membrane trafficking from the lateral border recycling compartment. J Exp Med 2008, 205:951-66.

[A7] Feng D, Nagy J A, Hipp J, Dvorak H F, Dvorak A M: Vesiculo-vacuolar organelles and the regulation of venule permeability to macromolecules by vascular permeability factor, histamine, and serotonin. J Exp Med 1996, 183: 1981-6.

[A8] Sullivan D P, Muller W A: Neutrophil and monocyte recruitment by PECAM, CD99, and other molecules via the LBRC. Seminars in immunopathology 2014, 36:193-209.

[A9] Feng G, Sullivan D P, Han F, Muller W A: Segregation of V E-cadherin from the LBRC depends on the ectodomain sequence required for homophilic adhesion. Journal of cell science 2015, 128:576-88.

[A10] Sullivan D P, Seidman M A, Muller W A: Poliovirus receptor (CD155) regulates a step in transendothelial migration between PECAM and CD99. Am J Pathol 2013, 182:1031-42.

[A11] Mamdouh Z, Mikhailov A, Muller W A: Transcellular migration of leukocytes is mediated by the endothelial lateral border recycling compartment. J Exp Med 2009, 206:2795-808.

[A12] Rodionov V I, Gyoeva F K, Gelfand V I: Kinesin is responsible for centrifugal movement of pigment granules in melanophores. Proc Natl Acad Sci USA 1991, 88:4956-60.

[A13] Bloom G S, Wagner M C, Pfister K K, Brady S T: Native structure and physical properties of bovine brain kinesin and identification of the ATP-binding subunit polypeptide. Biochemistry 1988, 27:3409-16.

[A14] Hirokawa N, Pfister K K, Yorifuji H, Wagner M C, Brady S T, Bloom G S: Submolecular domains of bovine brain kinesin identified by electron microscopy and monoclonal antibody decoration. Cell 1989, 56:867-78.

[A15] Gindhart J G, Jr., Desai C J, Beushausen S, Zinn K, Goldstein L S: Kinesin light chains are essential for axonal transport in *Drosophila*. The Journal of cell biology 1998, 141:443-54.

[A16] Glater E E, Megeath L J, Stowers R S, Schwarz T L: Axonal transport of mitochondria requires milton to recruit kinesin heavy chain and is light chain independent. The Journal of cell biology 2006, 173:545-57.

[A17] Rice S E, Gelfand V I: Paradigm lost: milton connects kinesin heavy chain to miro on mitochondria. The Journal of cell biology 2006, 173:459-61.

[A18] Muller W A, Ratti C M, McDonnell S L, Cohn Z A: A human endothelial cell-restricted, externally disposed plasmalemmal protein enriched in intercellular junctions. J Exp Med 1989, 170:399-414.

[A19] Muller W A, Weigl S: Monocyte-selective transendothelial migration: Dissection of the binding and transmigration phases by an in vitro assay. J Exp Med 1992, 176:819-28.

[A20] Wright S D, Rao P E, Van Voorhis W C, Craigmyle L S, Lida K, Talle M A, Westberg E F, Goldstein G, Silverstein S C: Identification of the C3bi receptor of human monocytes and macrophages by using monoclonal antibodies. Proceedings of the National Academy of Science 1983, 80:5699-703.

[A21] Muller W A, Weigl S A, Deng X, Phillips D M: PECAM-1 is required for transendothelial migration of leukocytes. J Exp Med 1993, 178:449-60.

[A22] Anisman H, Baines M G, Berczi I, Bernstein C N, Blennerhassett M G, Gorczynski R M, Greenberg A H, Kisil F T, Mathison R D, Nagy E, Nance D M, Perdue M H, Pomerantz D K, Sabbadini E R, Stanisz A, Warrington R J: Neuroimmune mechanisms in health and disease: 2. Disease. Cmaj 1996, 155:1075-82.

[A23] Liao F, Huynh H K, Eiroa A, Greene T, Polizzi E, Muller W A: Migration of monocytes across endothelium and passage through extracellular matrix involve separate molecular domains of PECAM-1. J Exp Med 1995, 182:1337-43.

[A24] Hirokawa N, Noda Y, Tanaka Y, Niwa S: Kinesin superfamily motor proteins and intracellular transport. Nat Rev Mol Cell Biol 2009, 10:682-96.

[A25] Lawrence C J, Dawe R K, Christie K R, Cleveland D W, Dawson S C, Endow S A, Goldstein L S, Goodson H V, Hirokawa N, Howard J, Malmberg R L, McIntosh J R, Miki H, Mitchison T J, Okada Y, Reddy A S, Saxton W M, Schliwa M, Scholey J M, Vale R D, Walczak C E, Wordeman L: A standardized kinesin nomenclature. J Cell Biol 2004, 167:19-22.

[A26] Hirokawa N: From electron microscopy to molecular cell biology, molecular genetics and structural biology: intracellular transport and kinesin superfamily proteins, KIFs: genes, structure, dynamics and functions. Journal of Electron Microscopy 2011, 60: S63-S92.

[A27] Ingold A L, Cohn S A, Scholey J M: Inhibition of kinesin-driven microtubule motility by monoclonal antibodies to kinesin heavy chains. The Journal of cell biology 1988, 107:2657-67.

[A28] Kanai Y, Okada, Y., Tanaka, Y., Harada, A., Terada, S., Hirokawa, N.: KIF5C, a novel neuronal kinesin enriched in motor neurons. J Neurosci 2000, 20:6374-84.

[A29] Jaulin F, Xue X, Rodriguez-Boulan E, Kreitzer G: Polarization-dependent selective transport to the apical membrane by KIF5B in MDCK cells. Dev Cell 2007, 13:511-22.

[A30] Krylyshkina O, Kaverina I, Kranewitter W, Steffen W, Alonso M C, Cross R A, Small J V: Modulation of substrate adhesion dynamics via microtubule targeting requires kinesin-1. The Journal of cell biology 2002, 156:349-59.

[A31] Daire V, Giustiniani J, Leroy-Gori I, Quesnoit M, Drevensek S, Dimitrov A, Perez F, Pous C: Kinesin-1 regulates microtubule dynamics via a c-Jun N-terminal kinase-dependent mechanism. The Journal of biological chemistry 2009, 284:31992-2001.

[A32] Cole D G, Chinn S W, Wedaman K P, Hall K, Vuong T, Scholey J M: Novel heterotrimeric kinesin-related protein purified from sea urchin eggs. Nature 1993, 366: 268-70.

[A33] Aizawa H, Sekine Y, Takemura R, Zhang Z, Nangaku M, Hirokawa N: Kinesin family in murine central nervous system. The Journal of cell biology 1992, 119:1287-96.

[A34] Niclas J, Navone F, Hom-Booher N, Vale R D: Cloning and localization of a conventional kinesin motor expressed exclusively in neurons. Neuron 1994, 12:1059-72.

[A35] Rahman A, Friedman D S, Goldstein L S: Two kinesin light chain genes in mice. Identification and characterization of the encoded proteins. The Journal of biological chemistry 1998, 273:15395-403.

[A36] Junco A, Bhullar B, Tarnasky H A, van der Hoorn F A: Kinesin light-chain KLC3 expression in testis is restricted to spermatids. Biology of reproduction 2001, 64:1320-30.

[A37] Khodjakov A, Lizunova E M, Minin A A, Koonce M P, Gyoeva F K: A specific light chain of kinesin associates with mitochondria in cultured cells. Mol Biol Cell 1998, 9:333-43.

[A38] McCart A E, Mahony D, Rothnagel J A: Alternatively spliced products of the human kinesin light chain 1 (KNS2) gene. Traffic 2003, 4:576-80.

[A39] Diefenbach R J, Mackay J P, Armati P J, Cunningham A L: The C-terminal region of the stalk domain of ubiquitous human kinesin heavy chain contains the binding site for kinesin light chain. Biochemistry 1998, 37:16663-70.

[A40] Cyr J L, Pfister K K, Bloom G S, Slaughter C A, Brady S T: Molecular genetics of kinesin light chains: generation of isoforms by alternative splicing. Proceedings of the National Academy of Sciences of the United States of America 1991, 88:10114-8.

[A41] Wedaman K P, Knight A E, Kendrick-Jones J, Scholey J M: Sequences of sea urchin kinesin light chain isoforms. Journal of molecular biology 1993, 231:155-8.

[A42] Gindhart J G, Jr., Goldstein L S: Tetratrico peptide repeats are present in the kinesin light chain. Trends in biochemical sciences 1996, 21:52-3.

[A43] Gyoeva F K, Bybikova E M, Minin A A: An isoform of kinesin light chain specific for the Golgi complex. Journal of cell science 2000, 113 (Pt 11): 2047-54.

[A44] Woźniak M J, Allan, Victoria J.: Cargo selection by specific kinesin light chain 1 isoforms. EMBO J 2006, 25:5457-68

[A45] Liao G G G: Kinesin is a candidate for cross-bridging microtubules and intermediate filaments. Selective binding of kinesin to detyrosinated tubulin and vimentin. J Biol Chem 1998, 273:9797-803.

[A46] Morihara T, Hayashi N, Yokokoji M, Akatsu H, Silverman M A, Kimura N, Sato M, Saito Y, Suzuki T, Yanagida K, Kodama T S, Tanaka T, Okochi M, Tagami S, Kazui H, Kudo T, Hashimoto R, Itoh N, Nishitomi K, Yamaguchi-Kabata Y, Tsunoda T, Takamura H, Katayama T, Kimura R, Kamino K, Hashizume Y, Takeda M: Transcriptome analysis of distinct mouse strains reveals kinesin light chain-1 splicing as an amyloid-beta accumulation modifier. Proceedings of the National Academy of Sciences of the United States of America 2014, 111: 2638-43.

[A47] Inomata H, Nakamura Y, Hayakawa A, Takata H, Suzuki T, Miyazawa K, Kitamura N: A scaffold protein JIP-1b enhances amyloid precursor protein phosphorylation by JNK and its association with kinesin light chain 1. The Journal of biological chemistry 2003, 278:22946-55.

[A48] Kamal A, Stokin G B, Yang Z, Xia C H, Goldstein L S: Axonal transport of amyloid precursor protein is mediated by direct binding to the kinesin light chain subunit of kinesin-I. Neuron 2000, 28:449-59.

[B1] Wong S Y, Hynes R O. 2006. Lymphatic or hematogenous dissemination: how does a metastatic tumor cell decide? Cell cycle. 5 (8): 812-7. PMCID: 1459485.

[B2] Saxena M, Christofori G. 2013. Rebuilding cancer metastasis in the mouse. Mol Oncol. 7 (2): 283-96. PMCID: 5528417.

[B3] Strilic B, Offermanns S. 2017. Intravascular Survival and Extravasation of Tumor Cells. Cancer cell. 32 (3): 282-93.

[B4] Fidler I J. 1970. Metastasis: quantitative analysis of distribution and fate of tumor emboli labeled with 125 I-5-iodo-2'-deoxyuridine. Journal of the National Cancer Institute. 45 (4): 773-82.

[B5] Muller W A. 2016. Localized signals that regulate transendothelial migration. Current opinion in immunology. 38:24-9. PMCID: 4715928.

[B6] Winger R C, Koblinski J E, Kanda T, Ransohoff R M, Muller W A. 2014. Rapid remodeling of tight junctions during paracellular diapedesis in a human model of the blood-brain barrier. J Immunol. 193 (5): 2427-37. PMCID: PMC4138548.

[B7] Mamdouh Z, Kreitzer G E, Muller W A. 2008. Leukocyte transmigration requires kinesin-mediated microtubule-dependent membrane trafficking from the lateral border recycling compartment. J Exp Med. 205 (4): 951-66. PMCID: PMC2292231.

[B8] Mamdouh Z, Mikhailov A, Muller W A. 2009. Transcellular migration of leukocytes is mediated by the endothelial lateral border recycling compartment. J Exp Med 206 (11): 2795-808.

[B9] Mamdouh Z, Chen X, Pierini L M, Maxfield F R, Muller W A. 2003. Targeted recycling of PECAM from endothelial cell surface-connected compartments during diapedesis. Nature. 421:748-53.

[B10] Strilic B, Yang L, Albarran-Juarez J, Wachsmuth L, Han K, Muller U C, Pasparakis M, Offermanns S. 2016. Tumour-cell-induced endothelial cell necroptosis via death receptor 6 promotes metastasis. Nature. 536 (7615): 215-8.

[B11] Li B, Zhao W D, Tan Z M, Fang W G, Zhu L, Chen Y H. 2006. Involvement of Rho/ROCK signalling in small cell lung cancer migration through human brain microvascular endothelial cells. FEBS letters. 580 (17): 4252-60.

[B12] Aragon-Sanabria V, Pohler S E, Eswar V J, Bicrowski M, Gomez E W, Dong C. 2017. V E-Cadherin Disassembly and Cell Contractility in the Endothelium are Necessary for Barrier Disruption Induced by Tumor Cells. Scientific reports. 7:45835. PMCID: 5385522.

[B13] Feng G, Sullivan D P, Han F, Muller W A. 2015. Segregation of V E-cadherin from the LBRC depends on the ectodomain sequence required for homophilic adhesion. J Cell Sci. 128 (3): 576-88.

[B14] Dasgupta B, Dufour E, Mamdouh Z, Muller W. 2009. A novel and critical role for tyrosine 663 in PECAM trafficking and transendothelial migration. J Immunol. 182 (8): 5041-51.

[B15] Cyrus B F, Muller W A. 2016. A Unique Role for Endothelial Cell Kinesin Light Chain 1, Variant 1 in Leukocyte Transendothelial Migration. The American journal of pathology. 186 (5): 1375-86. PMCID: 4861765.

[B16] Woźniak M J, Allan V J. 2006. Cargo selection by specific kinesin light chain 1 isoforms. The EMBO Journal. 25 (23): 5457-68.

[B17] McCart A E, Mahony D, Rothnagel J A. 2003. Alternatively spliced products of the human kinesin light chain 1 (KNS2) gene. Traffic. 4 (8): 576-80.

[B18] Muller W A, Weigl S. 1992. Monocyte-selective transendothelial migration: Dissection of the binding and transmigration phases by an in vitro assay. J Exp Med. 176:819-28.

[B19] Muller W A, Luscinskas F W. 2008. Assays of transendothelial migration in vitro. Methods Enzymol. 443:155-76.

[B20] Weber E W, Han F, Tauseef M, Birnbaumer L, Mehta D, Muller W A. 2015. TRPC6 is the endothelial calcium channel that regulates leukocyte transendothelial migration during the inflammatory response. J Exp Med. 212 (11): 1883-99. PMCID: 4612081.

[B21] Watson R L, Buck J, Levin L R, Winger R C, Wang J, Arase H, Muller W A. 2015. Endothelial CD99 signals through soluble adenylyl cyclase and PKA to regulate leukocyte transendothelial migration. J Exp Med. 212 (7): 1021-41.

[B22] Wiley H E, Gonzalez E B, Maki W, Wu M T, Hwang S T. 2001. Expression of C C chemokine receptor-7 and regional lymph node metastasis of B16 murine melanoma. Journal of the National Cancer Institute. 93 (21): 1638-43.

[B23] Homey B, Muller A, Zlotnik A. 2002. Chemokines: agents for the immunotherapy of cancer? Nature reviews Immunology. 2 (3): 175-84.

The invention claimed is:

1. A composition comprising a peptide comprising a sequence of SEQ ID NO: 3 at least 8 residues in length and a cell-penetrating peptide sequence.

2. The composition of claim 1, wherein the peptide comprises the full length of SEQ ID NO: 3.

3. The composition of claim 1, wherein the peptide comprises a sequence of SEQ ID NO: 8.

4. The composition of claim 1, wherein the peptide comprises a sequence of SEQ ID NO: 5.

5. The composition of claim 1, wherein the peptide comprises a sequence of SEQ ID NO: 6.

6. The composition of claim 1, wherein the peptide comprises a sequence of SEQ ID NO: 7.

7. The composition of claim 1, wherein the peptide comprises a sequence of SEQ ID NO: 1.

8. The composition of claim 1, wherein the cell-penetrating peptide sequence is a trans-activating transcriptional activator (TAT) peptide.

9. The composition of claim 1, wherein the cell-penetrating peptide sequence is an antennapedia peptide.

10. The composition of claim 1, wherein the composition is formulated for parenteral administration.

11. The composition of claim 1, wherein the composition is formulated for intravenous administration.

12. The composition of claim 1, wherein the composition is formulated for oral administration.

* * * * *

SEQUENCE LISTING

```
<160> NUMBER OF SEQ ID NOS: 9

<210> SEQ ID NO 1
<211> LENGTH: 10
<212> TYPE: PRT
<213> ORGANISM: Homo sapiens

<400> SEQUENCE: 1

Met Arg Lys Met Lys Leu Gly Leu Val Asn
1               5                   10

<210> SEQ ID NO 2
<211> LENGTH: 149
<212> TYPE: PRT
<213> ORGANISM: Homo sapiens

<400> SEQUENCE: 2

Met His Ala Glu Glu Arg Glu Glu Cys Lys Gly Lys Gln Lys Asp Gly
```

```
                1               5                  10                  15
            Thr Ser Phe Gly Glu Tyr Gly Gly Trp Tyr Lys Ala Cys Lys Val Asp
                           20                  25                  30

Ser Pro Thr Val Thr Thr Thr Leu Lys Asn Leu Gly Ala Leu Tyr Arg
                           35                  40                  45

Arg Gln Gly Lys Phe Glu Ala Ala Glu Thr Leu Glu Glu Ala Ala Met
                           50                  55                  60

Arg Ser Arg Lys Gln Arg Ser Ile Ser Glu Ile Pro Lys Lys Ile Leu
             65                 70                  75                  80

Ser Ala Asn Gly Ser Asn His Phe Pro Leu Pro Gly Ser Gln Gly Leu
                                85                  90                  95

Asp Asn Val His Lys Gln Arg Val Ala Glu Val Leu Asn Asp Pro Glu
                          100                 105                 110

Asn Met Glu Lys Arg Arg Ser Arg Glu Ser Leu Asn Val Asp Val Val
                          115                 120                 125

Lys Tyr Glu Ser Gly Pro Asp Gly Gly Glu Glu Met Arg Lys Met Lys
                          130                 135                 140

Leu Gly Leu Val Asn
            145

<210> SEQ ID NO 3
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
<222> LOCATION: (5)..(5)
<223> OTHER INFORMATION: Xaa= R or K
<220> FEATURE:
<221> NAME/KEY: MISC_FEATURE
<222> LOCATION: (6)..(6)
<223> OTHER INFORMATION: Xaa= I, L, V, or A
<220> FEATURE:
<221> NAME/KEY: MISC_FEATURE
<222> LOCATION: (7)..(7)
<223> OTHER INFORMATION: Xaa= G or A
<220> FEATURE:
<221> NAME/KEY: MISC_FEATURE
<222> LOCATION: (8)..(9)
<223> OTHER INFORMATION: Xaa= I, L, V, or A
<220> FEATURE:
<221> NAME/KEY: MISC_FEATURE
<222> LOCATION: (10)..(10)
<223> OTHER INFORMATION: Xaa= N or Q

<400> SEQUENCE: 3

Met Xaa Xaa Met Xaa Xaa Xaa Xaa Xaa Xaa
 1               5                  10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
```

```
<222> LOCATION: (5)..(5)
<223> OTHER INFORMATION: Xaa= R or K

<400> SEQUENCE: 4

Met Xaa Xaa Met Xaa Leu Gly Leu Val Asn
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa= I, L, V, or A
<220> FEATURE:
<221> NAME/KEY: MISC_FEATURE
<222> LOCATION: (8)..(9)
<223> OTHER INFORMATION: Xaa= I, L, V, or A

<400> SEQUENCE: 5

Met Arg Lys Met Lys Xaa Gly Xaa Xaa Asn
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa= R or K
<220> FEATURE:
<221> NAME/KEY: MISC_FEATURE
<222> LOCATION: (10)..(10)
<223> OTHER INFORMATION: Xaa= N or Q

<400> SEQUENCE: 6

Met Xaa Xaa Met Lys Leu Gly Leu Val Xaa
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa= I, L, V, or A
<220> FEATURE:
<221> NAME/KEY: MISC_FEATURE
<222> LOCATION: (8)..(9)
<223> OTHER INFORMATION: Xaa= I, L, V, or A
<220> FEATURE:
<221> NAME/KEY: MISC_FEATURE
<222> LOCATION: (10)..(10)
<223> OTHER INFORMATION: Xaa= N or Q

<400> SEQUENCE: 7

Met Arg Lys Met Lys Xaa Gly Xaa Xaa Xaa
1               5                   10

<210> SEQ ID NO 8
<211> LENGTH: 24
<212> TYPE: PRT
```

```
<213> ORGANISM: Artificial sequence
<220> FEATURE:
<223> OTHER INFORMATION: Synthetic peptide

<400> SEQUENCE: 8

Tyr Gly Arg Lys Lys Arg Arg Gln Arg Arg Gly Gly Gly Met Arg
1               5                   10                  15

Lys Met Lys Leu Gly Leu Val Asn
            20

<210> SEQ ID NO 9
<211> LENGTH: 24
<212> TYPE: PRT
<213> ORGANISM: Artificial sequence
<220> FEATURE:
<223> OTHER INFORMATION: Synthetic peptide

<400> SEQUENCE: 9

Tyr Gly Arg Lys Lys Arg Arg Gln Arg Arg Gly Gly Gly Gly Lys
1               5                   10                  15

Leu Asn Lys Met Val Met Leu Arg
            20
```